(12) United States Patent
Kick et al.

(10) Patent No.: US 7,569,725 B2
(45) Date of Patent: Aug. 4, 2009

(54) ANTHRANILIC ACID DERIVATIVES AS INHIBITORS OF 17β-HYDROXYSTEROID DEHYDROGENASE 3

(75) Inventors: Ellen K. Kick, Ewing, NJ (US); R. Michael Lawrence, Yardley, PA (US); Brian E. Fink, Princeton Junction, NJ (US); Raj N. Misra, Hopewell, NJ (US); Gregory D. Vite, Titusville, NJ (US)

(73) Assignee: Britsol-Myers Squibb Company, Princeton, NJ (US)

( * ) Notice: Subject to any disclaimer, the term of this patent is extended or adjusted under 35 U.S.C. 154(b) by 391 days.

(21) Appl. No.: 11/255,484

(22) Filed: Oct. 21, 2005

(65) Prior Publication Data

US 2006/0135619 A1 Jun. 22, 2006

Related U.S. Application Data

(60) Provisional application No. 60/620,705, filed on Oct. 21, 2004.

(51) Int. Cl.
C07C 237/40 (2006.01)
C07D 213/40 (2006.01)
A61K 31/166 (2006.01)

(52) U.S. Cl. .................. 564/155; 546/250; 514/621
(58) Field of Classification Search .................. 435/184; 436/64; 564/155
See application file for complete search history.

(56) References Cited

U.S. PATENT DOCUMENTS

| | | | |
|---|---|---|---|
| 3,646,202 A | 2/1972 | Mrozik et al. | |
| 4,971,957 A | 11/1990 | Tsutsumi et al. | |
| 6,251,917 B1 | 6/2001 | Lubisch et al. | |
| 6,297,375 B1 | 10/2001 | Bös et al. | |
| 7,056,918 B2 | 6/2006 | Dombroski et al. | |
| 7,173,031 B2 | 2/2007 | Borzilleri et al. | |
| 7,348,431 B2 | 3/2008 | Kim | |
| 7,378,415 B2 | 5/2008 | Sethofer et al. | |
| 2002/0014178 A1 | 2/2002 | Haught et al. | |
| 2004/0110832 A1 | 6/2004 | Mjalli et al. | |
| 2005/0191707 A1 | 9/2005 | Lorenzi et al. | |
| 2005/0192310 A1 | 9/2005 | Gavai et al. | |
| 2005/0250753 A1 | 11/2005 | Fink et al. | |

FOREIGN PATENT DOCUMENTS

| | | |
|---|---|---|
| JP | 2003/212834 | 7/2003 |
| WO | WO 99/46279 | 9/1999 |
| WO | WO 03/022835 | 3/2003 |
| WO | WO 03/075907 | 9/2003 |
| WO | WO 2004/006858 | 1/2004 |

OTHER PUBLICATIONS

RN 67796-13-8, STN international, HCAPLUS database, Accession No. 1978 : 563528.*
RN 55390-91-5, STN international, HCAPLUS database, Accession No. 1975: 140038.*
RN 70553-46-7, STN international, HCAPLUS database, Accession No. 1979: 405478.*
RN 131541-45-2, STN international, HCAPLUS database, Accession No. 1991: 62025.*
Maltais, R. et al., "Synthesis and Optimization of a New Family of Type 3 17β-Hydroxysteroid Dehydrogenase Inhibitors by Parallel Liquid-Phase Chemistry", J. Med. Chem., vol. 45, pp. 640-653 (2002).
Pittaway, D. E., "Inhibition of Testosterone Synthesis in the Canine Testis In Vitro", Contraception, vol. 27, No. 4, pp. 431-436 (1983).
Varnavas, A. et al., "C-terminal anthranoyl-anthranilic acid derivatives and their evaluation on CCK receptors", Il Farmaco 55, pp. 293-302 (2000).
Varnavas, A. et al., "Synthesis of N-terminal substituted anthranilic acid dimmer derivatives for evaluation on CCK receptors", Il Farmaco 56, pp. 555-564 (2001).

* cited by examiner

*Primary Examiner*—Shafiqul Haq
(74) *Attorney, Agent, or Firm*—Gary D. Greenblatt

(57) ABSTRACT

Disclosed are anthranilic acid derivatives having Formula (I):

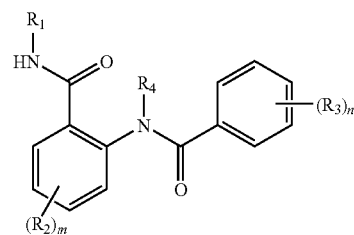

and pharmaceutically acceptable salts thereof; and pharmaceutical compositions comprising such compounds. Also disclosed are methods of using such compounds in the treatment of conditions or diseases such as prostate cancer, and methods of using such compounds in the inhibition of 17β-hydroxysteroid dehydrogenase type 3 enzyme.

9 Claims, No Drawings

ANTHRANILIC ACID DERIVATIVES AS INHIBITORS OF 17β-HYDROXYSTEROID DEHYDROGENASE 3

RELATED APPLICATIONS

This application claims priority benefit under Title 35 § 119(e) of U.S. provisional Application No. 60/620,705, filed Oct. 21, 2004, the contents of which are hereby incorporated herein by reference.

FIELD OF THE INVENTION

The present invention relates to anthranilic acid derivatives, to methods of using such compounds in the treatment of hormone sensitive diseases such as prostate cancer, and to pharmaceutical compositions containing such compounds.

BACKGROUND OF THE INVENTION

17β-hydroxysteroid dehydrogenase 3 (17β-HSD3) is an essential enzyme in the biosynthesis of testosterone. It catalyzes the reduction of androstenedione, a weakly active androgen produced by the adrenal glands, to testosterone. Inano et al., *Steroids*, 48, 1-26, (1986) and Luu-The et al., *J. Steroid Biochem. Mol. Biol.*, 55, 581-587 (1995). 17β-HSD3 is expressed predominately in the adult testes and to a lesser extent in seminal vesicles and prostate tissue, an expression pattern consistent with an enzyme involved in both gonadal and peripheral target tissue androgen biosynthesis. 17β-HSD3 is responsible for the synthesis of about 60% of all active androgens in men. Labrie, *Mol. Cell. Endocrinol.* 78, C113-C118 (1991). The development and progression of hormone sensitive diseases, e.g., prostate cancer, is stimulated by androgens such as testosterone. Inhibition of 17β-HSD3 therefore provides a novel means to disrupt testosterone biosynthesis for the treatment of androgen-associated diseases. Van Weerden et al., *J. Steroid Biochem. Mol. Biol.*, 20, 903-907 (1990) and Liu et al., *J. Clin. Endocrinol.*, 77, 1472-1478 (1993).

Current pharmacological treatments to prevent androgen action in androgen-associated diseases such as prostate cancer are centered on the combined use of luteinizing hormone releasing hormone (LHRH) analogues with androgen receptor antagonists ("anti-androgens"). Labrie et al., *Endocr.-Relat. Cancer*, 3, 243-278 (1996); Gheiler et al., *World J. Urol.*, 18, 190-193 (2000); and Simard, et al., *J. Urol.*, 49, 580-586 (1997). LHRH analogues interfere with central nervous system feedback mechanisms to suppress testosterone biosynthesis in the testes to produce chemical castration. However, it is estimated that up to 50% of testosterone levels remain within prostate tissue following chemical or surgical castration indicating the existence of alternate routes of testosterone biosynthesis independent of the testes. Anti-androgens are used to block the action of this remaining testosterone in prostate cancer cells by antagonizing hormone function at the level of receptor binding. Although the combined use of LHRH analogues with anti-androgens has shown success in the management of prostate cancer, these responses are largely restricted to advanced metastatic disease. Further, patients receiving these treatments ultimately become refractory and progress to a more aggressive, hormone-independent state for which there is no effective therapy.

Inhibitors of 17β-HSD3 have been described in the art. See, e.g., Pittaway, *Contraception*, 27, 431 (1983); Labrie et al., WO99/46279; Maltais et al., *J. Med. Chem.*, 45, 640-653 (2002); and Guzi et al., WO03/022835.

In addition, co-pending patent application Ser. No. 11/066,373, filed Feb., 25-2005; and U.S. Patent Application Publication No. US 2005/192310, published Sep. 1, 2005, disclose fused tricyclic compounds and fused heterotricyclic compounds, respectively, as 17β-HSD3 inhibitors, the disclosures of which are both hereby incorporated herein by reference.

The compounds of the present invention are inhibitors of 17β-HSD3, and therefore have therapeutic use as anti-cancer agents, as well as other therapeutic agents, for example, as anti-fertility agents.

SUMMARY OF THE INVENTION

The present invention provides an anthranilic acid derivatives of the following Formula I, or a tautomer, a pharmaceutically acceptable salt or solvate thereof, which compounds are especially useful as inhibitors of 17β-hydroxysteroid dehydrogenase 3 (17β-HSD3):

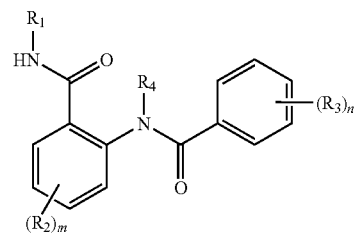

I or a pharmaceutically acceptable salt or solvate thereof, wherein:

$R_1$ is substituted alkyl or substituted cycloalkyl;

Each $R_2$ is independently selected from H, alkyl, substituted alkyl, and $OR_{11}$; or one $R_2$ together with another adjacent $R_2$ may form a fused phenyl ring;

Each $R_3$ is independently selected from H, halogen, OH, OMe, OEt, SH, Me, Et, $CO_2H$, $NHSO_2Me$, and $NHSO_2Et$; or one $R_3$ together with another adjacent $R_3$ may form a fused heterocycle;

$R_4$ is H, Me, Et, or iso-propyl;

$R_{11}$ is H, alkyl, substituted alkyl, cycloalkyl, substituted cycloalkyl, aryl, or substituted aryl;

m is 1 or 2; and n is 1, 2, or 3.

The present invention also relates to methods of using compounds of Formula I to treat hormone sensitive diseases, such as, for example, prostate cancer, and pharmaceutical compositions containing such compounds.

The present invention also relates to at least one Formula (I) compound selected from:

2-[(3-chloro-4-hydroxybenzoyl)amino]-N-[2-(2-methoxyphenyl)ethyl]-5-phenoxybenzamide;

2-[(3-chloro-4-hydroxybenzoyl)amino]-N-[2-(2-methoxyphenyl)ethyl]-5-phenoxybenzamide;

3-chloro-4-hydroxy-N-[2-({[2-(2-methoxyphenyl)ethyl]amino}carbonyl)phenyl]benzamide;

2-[(3-chloro-4-hydroxybenzoyl)amino]-N-ethyl-5-phenoxybenzamide;

2-[(3-chloro-4-hydroxybenzoyl)amino]-N-[2-(2-chlorophenyl)ethyl]-5-phenoxybenzamide;

3-chloro-N-{2-[(ethylamino)carbonyl]phenyl}-4-hydroxybenzamide;

3-chloro-4-hydroxy-N-(2-{[(2-phenylethyl)amino]carbonyl}phenyl)benzamide;
3-chloro-N-[2-({[2-(2-chlorophenyl)ethyl]amino}carbonyl)phenyl]-4-hydroxybenzamide;
2-[(3-chloro-4-hydroxybenzoyl)amino]-5-phenoxy-N-(2-phenylethyl)benzamide;
2-[(3-chloro-4-hydroxybenzoyl)amino]-N-isopropyl-5-methoxybenzamide;
2-[(3-chloro-4-hydroxybenzoyl)amino]-N-isobutyl-5-phenoxybenzamide;
2-[(3-chloro-4-hydroxybenzoyl)amino]-N-[2-(4-methoxyphenyl)ethyl]-5-phenoxybenzamide;
2-[(3-chloro-4-hydroxybenzoyl)amino]-N-[2-(3-methoxyphenyl)ethyl]-5-phenoxybenzamide;
3-chloro-4-hydroxy-N-[2-({[2-(3-methoxyphenyl)ethyl]amino}carbonyl)phenyl]benzamide;
3-chloro-4-hydroxy-N-[2-({[2-(4-methoxyphenyl)ethyl]amino}carbonyl)phenyl]benzamide;
3-chloro-N-[2-({[2-(3-chlorophenyl)ethyl]amino}carbonyl)phenyl]-4-hydroxybenzamide;
2-[(3-chloro-4-hydroxybenzoyl)amino]-5-phenoxy-N-(2-pyridin-2-ylethyl)benzamide;
2-[(3-chloro-4-hydroxybenzoyl)amino]-5-phenoxy-N-(1-phenylethyl)benzamide;
2-[(3-chloro-4-hydroxybenzoyl)amino]-N-isopropyl-5-phenoxybenzamide;
2-[(3-chloro-4-hydroxybenzoyl)amino]-N-[2-(4-chlorophenyl)ethyl]-5-phenoxybenzamide;
2-[(3-chloro-4-hydroxybenzoyl)amino]-5-phenoxy-N-propylbenzamide;
2-[(3-chloro-4-hydroxybenzoyl)amino]-5-methoxy-N-[2-(2-methoxyphenyl)ethyl]benzamide;
2-[(3-chloro-4-hydroxybenzoyl)amino]-5-phenoxy-N-(2-phenylpropyl)benzamide;
2-[(3-chloro-4-hydroxybenzoyl)amino]-N-[2-(3-chlorophenyl)ethyl]-5-phenoxybenzamide;
2-[(4-hydroxy-3-methylbenzoyl)amino]-N-isopropyl-5-phenoxybenzamide;
N-[2-(2-chlorophenyl)ethyl]-2-[(4-hydroxybenzoyl)amino]-5-phenoxybenzamide;
2-[(4-hydroxybenzoyl)amino]-N-isopropyl-5-phenoxybenzamide;
N-[2-(4-chlorophenyl)ethyl]-2-[(3-hydroxybenzoyl)amino]-5-phenoxybenzamide;
2-[(3-chloro-4-hydroxybenzoyl)amino]-4,5-dimethoxy-N-[2-(2-methoxyphenyl)ethyl]benzamide;
4-[({2-[(isopropylamino)carbonyl]-4-phenoxyphenyl}amino)carbonyl]benzoic acid;
2-[(3-chloro-4-hydroxybenzoyl)amino]-N-[2-(2-methoxyphenyl)ethyl]-4-methylbenzamide;
3-[(3-chloro-4-hydroxybenzoyl)amino]-N-isopropyl-2-naphthamide;
3-[(2-hydroxy-5-methylbenzoyl)amino]-N-1,2,3,4-tetrahydronaphthalen-1-yl-2-naphthamide;
3-[({2-[(isopropylamino)carbonyl]-4-phenoxyphenyl}amino)carbonyl]benzoic acid;
N-isopropyl-2-({4-[(methylsulfonyl)amino]benzoyl}amino)-5-phenoxybenzamide;
3-chloro-4-hydroxy-N-{2-[(isopropylamino)carbonyl]-4-phenoxyphenyl}-5-methylbenzamide;
N-isopropyl-2-[(4-mercaptobenzoyl)amino]-5-phenoxybenzamide;
3,5-dichloro-4-hydroxy-N-{2-[(isopropylamino)carbonyl]-4-phenoxyphenyl}benzamide;
N-{2-[(isopropylamino)carbonyl]-4-phenoxyphenyl}-1H-indole-5-carboxamide;
2-[(3-chlorobenzoyl)amino]-N-isopropyl-5-phenoxybenzamide;
2-[(3-chloro-4-hydroxybenzoyl)(methyl)amino]-N-isopropyl-5-phenoxybenzamide;
2-[(3-chloro-4-methoxybenzoyl)amino]-5-phenoxy-N-(2-phenylethyl)benzamide;
3-chloro-4-methoxy-N-(2-{[(2-phenylethyl)amino]carbonyl}phenyl)benzamide; and
2-[(3-chloro-4-hydroxybenzoyl)amino]-N-[2-(2-methoxyphenyl)ethyl]-5-methylbenzamide.

FURTHER DESCRIPTION OF THE INVENTION

The features and advantages of the present invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof.

Unless specifically stated otherwise herein, references made in the singular may also include the plural. For example, "a" and "an" may refer to either one, or one or more.

The definitions set forth herein take precedence over definitions set forth in any patent, patent application, and/or patent application publication incorporated herein by reference.

The following are definitions of terms used in the present specification. The initial definition provided for a group or term herein applies to that group or term throughout the present specification individually or as part of another group, unless otherwise indicated.

The terms "alkyl" and "alk" refers to a straight or branched chain alkane (hydrocarbon) radical containing from 1 to 12 carbon atoms, preferably 1 to 6 carbon atoms. Exemplary "alkyl" groups include, but are nor limited to, for example, methyl, ethyl, propyl, isopropyl, n-butyl, t-butyl, isobutyl pentyl, hexyl, isohexyl, heptyl, 4,4-dimethylpentyl, octyl, 2,2,4-trimethylpentyl, nonyl, decyl, undecyl, and dodecyl.

The term "$C_1$-$C_4$ alkyl" refers to a straight or branched chain alkane (hydrocarbon) radical containing from 1 to 4 carbon atoms, such as, for example, methyl, ethyl, propyl, isopropyl, n-butyl, t-butyl, and isobutyl.

The term "substituted alkyl" refers to an alkyl group substituted with one or more substituents, preferably 1 to 4 substituents, at any available point of attachment. Exemplary substituents include, but are not limited to, for example, one or more of the following groups: halogen (e.g., a single halogen substituent or multiple halo substitutents forming, in the latter case, groups such as $CF_3$ or an alkyl group bearing $Cl_3$), cyano, nitro, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein $R_a$ is hydrogen, alkyl, cycloalkyl, alkenyl, cycloalkenyl, alkynyl, heterocycle, or aryl; $R_b$, $R_c$ and $R_d$ are independently hydrogen, alkyl, cycloalkyl, heterocycle, aryl, or said $R_b$ and $R_c$ together with the N to which they are bonded optionally form a heterocycle; and $R_e$ is alkyl, cycloalkyl, alkenyl, cycloalkenyl, alkynyl, heterocycle, or aryl. In the aforementioned exemplary substitutents, groups such as alkyl, cycloalkyl, alkenyl, alkynyl, cycloalkenyl, heterocycle, and aryl can themselves be optionally substituted.

The term "cycloalkyl" refers to a fully saturated cyclic hydrocarbon group containing from 1 to 4 rings and 3 to 8 carbons per ring. Exemplary such groups include, but are not limited to, for example, cyclopropyl, cyclobutyl, cyclopentyl, cyclohexyl, and cycloheptyl.

The term "substituted cycloalkyl" refers to a cycloalkyl group substituted with one or more substituents, preferably 1 to 4 substituents, at any available point of attachment. Exemplary substituents include, but are not limited to, for example, nitro, cyano, alkyl, substituted alkyl, and the groups recited above as exemplary alkyl substituents. Exemplary substituents also include, but are not limited to, for example, spiro-attached or fused cylic substituents, especially spiro-attached cycloalkyl, spiro-attached cycloalkenyl, spiro-attached heterocycle (excluding heteroaryl), fused cycloalkyl, fused cycloalkenyl, fused heterocycle, and fused aryl, wherein the aforementioned cycloalkyl, cycloalkenyl, heterocycle and aryl substitutents can themselves be optionally substituted.

The term "aryl" refers to cyclic, aromatic hydrocarbon groups that have 1 to 5 aromatic rings, especially monocyclic or bicyclic groups such as, for example, phenyl, biphenyl, and naphthyl. When containing two or more aromatic rings (bicyclic, etc.), the aromatic rings of the aryl group may be joined at a single point (e.g., biphenyl), or fused (e.g., naphthyl and phenanthrenyl).

The term "substituted aryl" refers to an aryl group substituted by one or more substituents, preferably 1 to 3 substituents, at any point of attachment. Exemplary substituents include, but are not limited to, for example, nitro, cycloalkyl, substituted cycloalkyl, cycloalkenyl, substituted cycloalkenyl, cyano, alkyl, substituted alkyl, and the groups recited above as exemplary alkyl substituents. Exemplary substituents also include, but are not limited to, for example, fused cylic groups, especially fused cycloalkyl, fused cycloalkenyl, fused heterocycle, and fused aryl, wherein the aforementioned cycloalkyl, cycloalkenyl, heterocycle, and aryl substituents can themselves be optionally substituted.

The terms "heterocycle" and "heterocyclic" refer to fully saturated, or partially or fully unsaturated, including aromatic (i.e., "heteroaryl") cyclic groups, such as, for example, 4 to 7 membered monocyclic, 7 to 11 membered bicyclic, or 10 to 16 membered tricyclic ring systems that have at least one heteroatom in at least one carbon atom-containing ring. Each ring of the heterocyclic group containing a heteroatom may have 1, 2, 3, or 4 heteroatoms selected from N, O, and/or S, where the N and S heteroatoms may optionally be oxidized and the N heteroatom may optionally be quaternized. For example, the term "heteroarylium" refers to a heteroaryl group bearing a quaternary nitrogen atom and thus a positive charge. The heterocyclic or heterocycle group may be attached via any heteroatom or carbon atom.

Exemplary monocyclic heterocycle or heterocyclic groups include, but are not limited to, for example, azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, hexahydrodiazepinyl, 4-piperidonyl, pyridyl, pyrazinyl, pyrimidinyl, pyridazinyl, triazinyl, triazolyl, tetrazolyl, tetrahydropyranyl, morpholinyl, thiamorpholinyl, thiamorpholinyl sulfoxide, thiamorpholinyl sulfone, 1,3-dioxolane, and tetrahydro-1,1-dioxothienyl.

Exemplary bicyclic heterocycle or heterocyclic groups include, but are not limited to, for example, indolyl, isoindolyl, benzothiazolyl, benzoxazolyl, benzoxadiazolyl, benzothienyl, quinuclidinyl, quinolinyl, tetrahydroisoquinolinyl, isoquinolinyl, benzimidazolyl, benzopyranyl, indolizinyl, benzofuryl, benzofurazanyl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), triazinylazepinyl, and tetrahydroquinolinyl.

Exemplary tricyclic heterocycle or heterocyclic groups include, but are not limited to, for example, carbazolyl, benzidolyl, phenanthrolinyl, acridinyl, phenanthridinyl, and xanthenyl.

The terms "substituted heterocycle" and "substituted heterocyclic" (such as "substituted heteroaryl") refer to heterocycle or heterocyclic groups substituted with one or more substituents, preferably 1 to 4 substituents, at any available point of attachment. Exemplary substituents include, but are not limited to, for example, cycloalkyl, substituted cycloalkyl, cycloalkenyl, substituted cycloalkenyl, nitro, oxo (i.e., =O), cyano, alkyl, substituted alkyl, and the groups recited above as exemplary alkyl substituents. Exemplary substituents also include, but are not limited to, for example, spiro-attached or fused cylic substituents at any available point or points of attachment, especially spiro-attached cycloalkyl, spiro-attached cycloalkenyl, spiro-attached heterocycle (excluding heteroaryl), fused cycloalkyl, fused cycloalkenyl, fused heterocycle, and fused aryl, where the aforementioned cycloalkyl, cycloalkenyl, heterocycle and aryl substituents can themselves be optionally substituted.

The term "quaternary nitrogen" refers to a tetravalent positively charged nitrogen atom including, for example, the positively charged nitrogen in a tetraalkylammonium group (e.g., tetramethylammonium, N-methylpyridinium), the positively charged nitrogen in protonated ammonium species (e.g., trimethyl-hydroammonium, N-hydropyridinium), the positively charged nitrogen in amine N-oxides (e.g., N-methyl-morpholine-N-oxide, pyridine-N-oxide), and the positively charged nitrogen in an N-amino-ammonium group (e.g., N-aminopyridinium).

The terms "halogen" or "halo" refer to chlorine, bromine, fluorine, or iodine.

The term "carbocyclic" refers to aromatic or non-aromatic 3 to 7 membered monocyclic and 7 to 11 membered bicyclic groups, in which all atoms of the ring or rings are carbon atoms.

"Substituted carbocyclic" refers to a carbocyclic group substituted with one or more substituents, preferably 1 to 4 substituents, at any available point of attachment. Exemplary substituents include, but are not limited to, for example, nitro, cyano, $OR_a$, wherein $R_a$ is as defined hereinabove, and the groups recited above as exemplary cycloalkyl substituents.

When a functional group is termed "protected", this means that the group is in modified form to mitigate, especially preclude, undesired side reactions at the protected site. Suitable protecting groups for the methods and compounds described herein include, without limitation, those described in standard textbooks, such as Greene, T. W. et al., *Protective Groups in Organic Synthesis*, Wiley, N.Y. (1999).

Unless otherwise indicated, any heteroatom with unsatisfied valences is assumed to have hydrogen atoms sufficient to satisfy the valences.

Throughout the specification, groups and substituents thereof may be chosen by one skilled in the field to provide stable moieties and compounds.

The compounds of Formula I can also form salt(s), which are within the scope of the present invention. The term "pharmaceutically acceptable salt(s)", as employed herein, includes acidic and/or basic salt(s) formed with inorganic and/or organic acids and bases, and such term, as used herein, further includes zwitterion(s) ("inner salts"). The terms "zwitterion(s)" and "zwitterion", as employed herein, denote compound(s) containing both a basic moiety, including but not limited to, for example, pyridine and imidazole; and an acidic moiety including but not limited to, for example, a carboxylic acid.

In general, pharmaceutically acceptable (i.e. non-toxic and physiologically acceptable) salts are preferred, but other salts can be used to isolate and/or purify the compounds of Formula I. Salts of the compounds of Formula I can be formed by, for example, reacting the Formula I compound with, for example, an equivalent amount of acid or base in a medium that allows the thusly formed salt to, for example, either be precipitated out, or be isolated via lyophilization.

Acidic salt(s) that can be formed from compounds of Formula (I) and inorganic and/or organic acids include, but are not limited to, for example, acetates, such as are formed with, for example, acetic acid and trihaloacetic acid, e.g., trifluoroacetic acid; adipates; alginates; ascorbates; aspartates; benzoates; benzenesulfonates; bisulfates; borates; butyrates; citrates; camphorates; camphorsulfonates; cyclopentanepropionates; digluconates; dodecylsulfates; ethanesulfonates; fumarates; glucoheptanoates; glycerophosphates; hemisulfates; heptanoates; hexanoates; hydrochlorides; hydrobromides; hydroiodides; hydroxyethanesulfonates, such as, for example, 2-hydroxyethanesulfonates; lactates; maleates; methanesulfonates; naphthalenesulfonates, such as, for example, 2-naphthalenesulfonates; nicotinates; nitrates; oxalates; pectinates; persulfates; phenylpropionates, such as, for example, 3-phenylpropionates; phosphates; picrates; pivalates; propionates; salicylates; succinates; sulfates, such as, for example, are formed with sulfuric acid; sulfonates; tartrates; thiocyanates; toluenesulfonates, such as, for example, tosylates; and undecanoates. Such salts can be formed in accordance with methods known to a person of ordinary skill in the art.

Basic salt(s) that can be formed from compounds of Formula (I) and inorganic and/or organic bases include, but are not limited to, for example, ammonium salts; alkali metal salts, such as, for example, sodium, lithium and potassium salts; alkaline earth metal salts, such as, for example, calcium and magnesium salts; salts with organic bases, such as, for example, organic amines, e,g., benzathines, dicyclohexylamines, hydrabamines (formed with, for example, N,N-bis (dehydroabietyl) ethylenediamine), N-methyl-D-glucamines, N-methyl-D-glycamides, and t-butyl amines; salts formed with amino acids, such as, for example, arginine and lysine; and salts formed by using agents, such as, for example, lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), and aralkyl halides (e.g. benzyl and phenethyl bromides) to quaternize basic nitrogen-containing groups. Such salts can be formed in accordance with methods known to a person of ordinary skill in the art.

Prodrug(s) of Formula I are further contemplated herein. The terms "prodrug" and "prodrug(s)", as employed herein, denotes a compound which, upon administration to a subject, undergoes chemical conversion by metabolic or chemical processes in vivo to yield a compound or derivative of Formula I, or a salt and/or solvate thereof. Various forms of prodrug(s) are well known in the art. For examples of such prodrug derivatives, see:

a) *Design of Prodrugs*, edited by H. Bundgaard, (Elsevier, 1985) and *Methods in Enzymology*, Vol. 112, pp. 309-396, edited by K. Widder et al. (Academic Press, 1985);

b) *A Textbook of Drug Design and Development*, edited by Krosgaard-Larsen and H. Bundgaard, Chapter 5, "Design and Application of Prodrugs," by H. Bundgaard, pp. 113-191 (1991); and c) H. Bundgaard, *Advanced Drug Delivery Reviews*, 8, pp. 1-38 (1992), each of which is incorporated herein by reference.

Solvates of the compounds of Formula I are also contemplated herein. Such solvates include, for example, hydrates. The term "solvate", as employed herein, denotes a compound produced by the chemical interaction of a solvent with a solute comprising Formula I compound.

The present invention contemplates all stereoisomers, such as, for example, those that may exist due to asymmetric carbons on various substituents, and geometric isomers of Formula I, either in admixture or in pure or substantially pure form. Specifically, the present invention contemplates all enantiomers, tautomers, and diastereomers of Formula I, as well as, mixtures, compounds, racemic compounds, racemic mixtures, and racemates produced therefrom. Even more particularly, the present invention contemplates all optically active isomers of Formula I, including pure or substantially pure optically active isomers, i.e., optically active isomers substantially free of other isomers. The chiral centers of the present invention can have the S or R configuration as defined by the IUPAC 1974 Recommendations.

When a compound containing a single enantiomer of Formula I is desired, such compound can be obtained by either resolution of the final product or by stereospecific synthesis from either isomerically pure starting material(s), or any convenient intermediate(s). Resolution of the final product, an intermediate, or a starting material can be effected by any suitable method known in the art, including, for example, physical methods, such as, for example, fractional crystallization, separation or crystallization of diastereomeric derivatives, and separation by chiral column chromatography. Individual optical isomers can be obtained from racemates through, for example, conventional methods, such as, for example, salt formation with an optically active acid followed by crystallization.

"Substantially pure" Formula I compounds are further contemplated herein as part of the present invention. The term "substantially pure" as used herein means the Formula I compounds produced herein may be further isolated and purified so as to produce a composition containing an amount by weight equal to or greater than 99% Formula I compound. The substantially pure Formula I compound can be used or Formulated as further described herein.

All configurational isomers of the compounds of the present invention are further contemplated, either in admixture, or in a pure or substantially pure form. The compounds of the present invention as defined embrace both cis (Z) and trans (E) alkene isomers, as well as cis and trans isomers of cyclic hydrocarbon or heterocyclic rings.

All numbers expressing quantities of ingredients, properties such as molecular weight, reaction conditions, and so forth that are preceded by the word "about" are to be understood as only approximations so that slight variations above and below the stated number may be used to achieve substantially the same results as the stated number. Accordingly, unless indicated to the contrary, numerical parameters preceded by the word "about" are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

It is to be understood that each of the variously stated ranges is intended to be continuous so as to include each numerical parameter between the stated minimum and maximum value of each range. It is to be further understood that, while not intending to limit the applicability of the doctrine of equivalents to the scope of the claims, each numerical parameter should at least be construed in a manner consistent with the reported number of significant digits for each numerical parameter and by applying ordinary rounding techniques. It is to be even further understood that, while not intending to limit the applicability of the doctrine of equivalents to the scope of the claims, even though a number may be contained within a numerical range wherein at least one of the minimum and maximum numbers of the range is or is not preceded by the word "about", each numerical value contained within the range may or may not be preceded by the word "about". For Example, a range of about 1 to about 10 includes about 1, about 2, 2, about 3, 3, about 4, 4, about 5, 5, about 6, 6, about 7, 7, about 8, 8, about 9, 9, and about 10; a range of about 1.1 to about 3.2 includes about 1.1, about 1.2, 1.2, about 1.3, 1.3, about 1.4, 1.4, about 1.5, 1.5, about 1.6, 1.6, about 1.7, 1.7, about 1.8, 1.8, about 1.9, 1.9, about 2.0, 2.0, about 2.1, 2.1, about 2.2, 2.2, about 2.3, 2.3, about 2.4, 2.4, about 2.5, 2.5, about 2.6, 2.6, about 2.7, 2.7, about 2.8, 2.8, about 2.9, 2.9, about 3.0, 3.0, about 3.1, 3.1, and about 3.2; and a range of about 1 to 4 includes about 1, 2, about 2, 3, about 3, and 4.

In general, the compounds of Formula I can be prepared in accordance with Schemes I to III and the general knowledge of one skilled in the art. Tautomers and solvates (e.g., hydrates) of the compounds of Formula I are also within the scope of the present invention. Methods of solvation are generally known in the art. Solvents, temperatures, pressures, and other reaction conditions can be readily selected by one of ordinary skill in the art. Starting materials are either commercially available, and/or readily prepared by one of ordinary skill in the art.

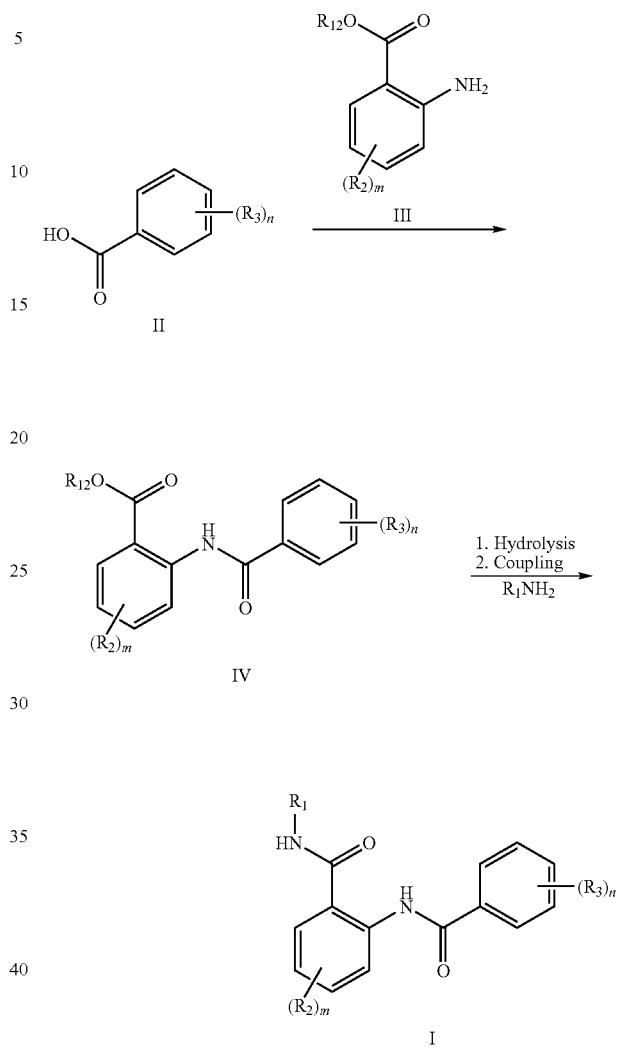

Scheme 1

In accordance with Scheme 1, $R_1$, $R_2$, $R_3$, m, and n are as defined hereinabove; and $R_{12}$ is a $C_1$-$C_4$ alkyl. When $R_3$ is OH, SH or $CO_2H$; or when $R_2$ is $OR_{11}$ and $R_{11}$ is H, it is desirable to protect $R_3$ and $R_{11}$ with a suitable protecting group, such as, for example, an ether or ester protecting group that can be removed after the last amide coupling step. Suitable protecting groups include, but are not limited to, for example, the protecting groups described in Greene, T. W. et al., *Protective Groups in Organic Synthesis*, Wiley, N.Y. (1999), and are further illustrated in Scheme 3 and the Examples.

Step 1

Compound IV can be produced either by reacting compound II with compound III under standard peptide coupling conditions, or alternatively, by reacting compound II with a chlorinating reagent, such as, for example, $(COCl)_2$ or $SOCl_2$ to convert compound II to an acid chloride, and then reacting the compound II acid chloride with compound III in the presence of a base.

Step 2

A compound in accordance with Formula I can be obtained by hydrolyzing compound IV, and then reacting hydrolyzed compound IV with $R_1NH_2$ under standard amide coupling conditions.

Step 3

A compound in accordance with Formula I can be obtained by coupling compound VII with compound II.

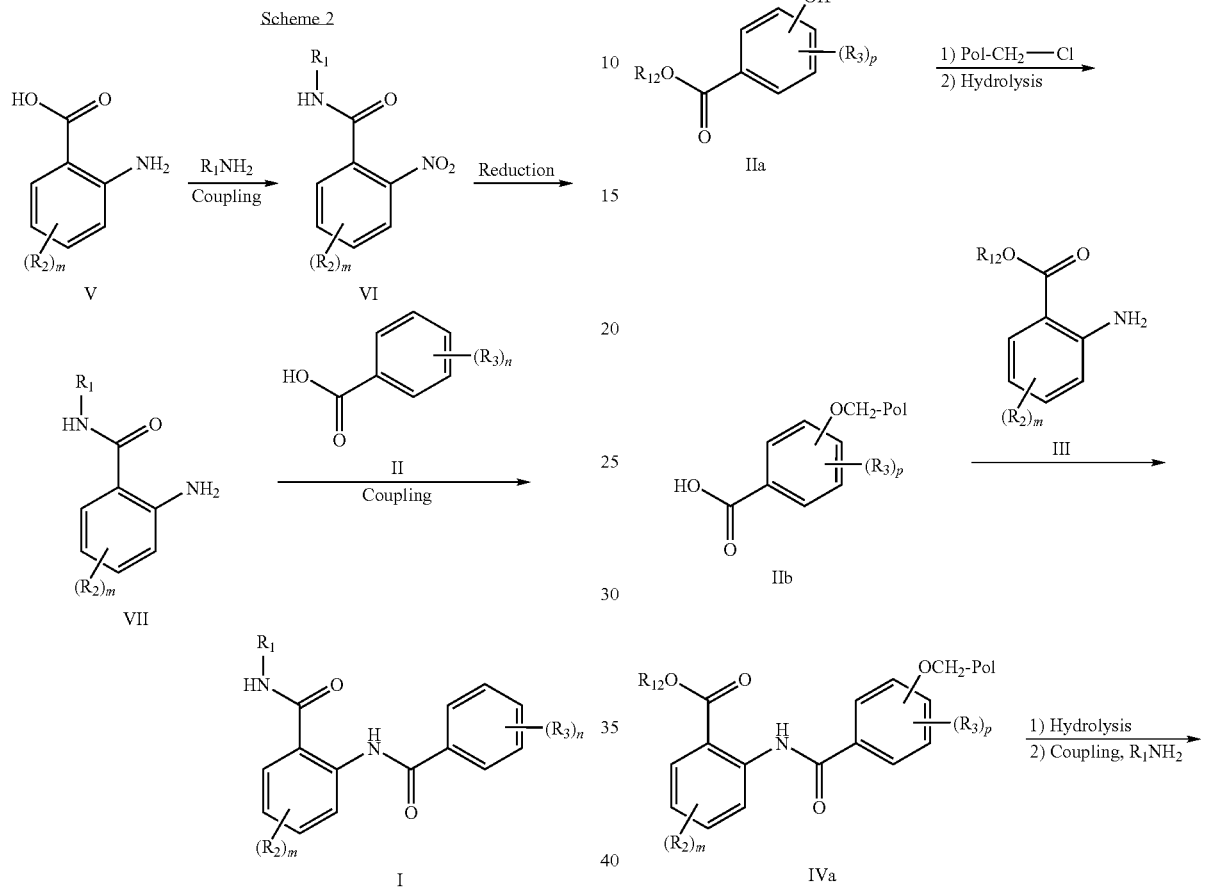

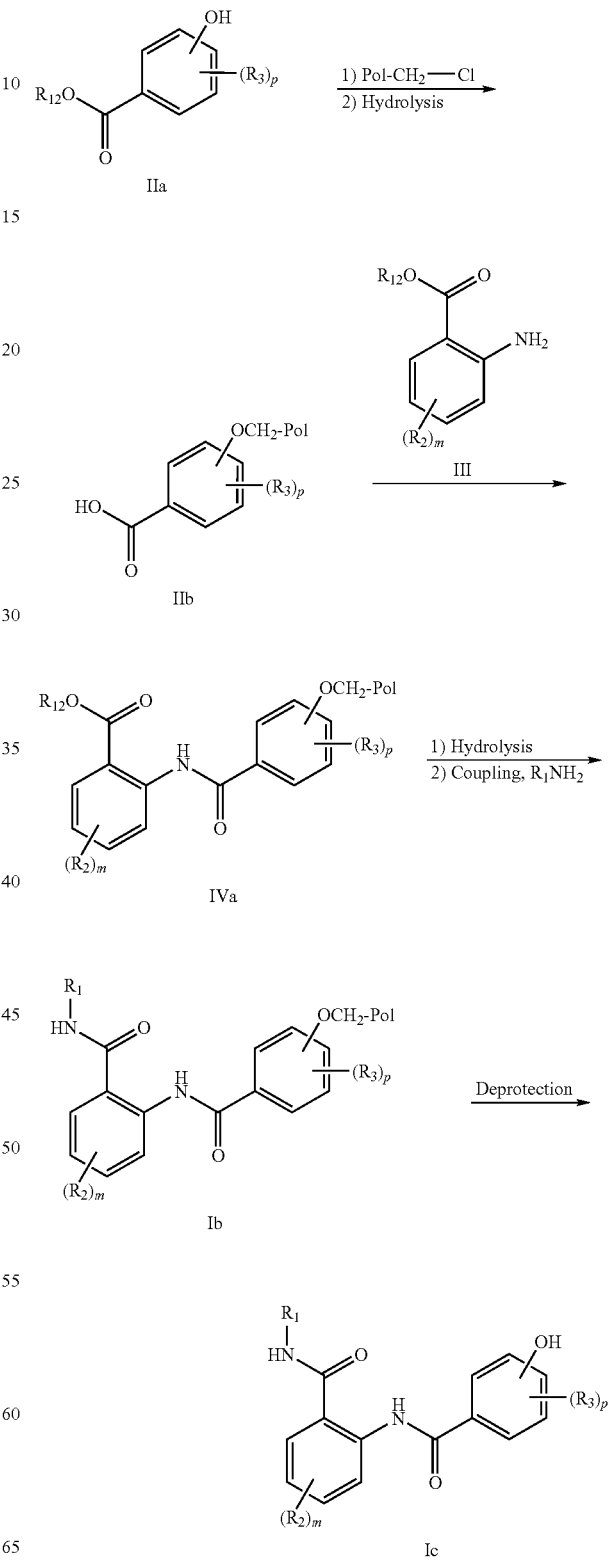

In accordance with Scheme 2, $R_1$, $R_2$, $R_3$, m, and n are as defined hereinabove. When $R_3$ is OH, SH or $CO_2H$; or when $R_2$ is $OR_{11}$ and $R_{11}$ is H, it is desirable to protect $R_3$ and $R_{11}$ with a suitable protecting group, such as, for example, an ether or ester protecting group that can be removed after the last amide coupling step. Suitable protecting groups include, but are not limited to, for example, the protecting groups described in Greene, T. W. et al., *Protective Groups in Organic Synthesis*, Wiley, N.Y. (1999), and are further illustrated in Scheme 3 and the Examples.

Step 1

Compound VI can be prepared either by reacting compound V with $R_1NH_2$ under standard peptide coupling conditions, or alternatively, by reacting compound V with a chlorinating reagent, such as, for example $(COCl)_2$ or $SOCl_2$, to convert compound V to an acid chloride, and then reacting the compound V acid chloride with $R_1NH_2$ in the presence of a base.

Step 2

Compound VII can be obtained by treating compound VI with a reducing reagent, such as, for example, tin(II) chloride.

A compound of Formula I having the structure of Formula Ic can be prepared according to Scheme 3 via library synthesis, wherein $R_1$, $R_2$, $R_3$, and m are as defined hereinabove; p is 1 or 2; Pol is polystyrene resin; and $R_{12}$ is a $C_1$-$C_4$ alkyl.

Step 1

Compound IIb can be obtained by reacting compound IIa with p-benzyloxybenzyl chloride polystyrene resin in the presence of a base, such as, for example, NaH, in an organic solvent, such as, for example, DMF, followed by hydrolysis.

Step 2

Compound IVa can be produced by reacting compound IIb with compound III under standard peptide coupling condition (e.g., DIC, HOAt, NMP; or NosCl, diisopropylethyl amine).

Step 3

Compound Ib can be obtained by hydrolyzing compound IVa to produce the corresponding acid, which can then be reacted with $R_1NH_2$.

Step 4

A compound in accordance with Formula Ic can be produced by treating compound Ib with an acid, such as, for example, TFA in dichloromethane, to remove the p-benzyloxybenzyl polystyrene resin.

Assays

Compounds within the scope of Formula I, including one or more of the compounds described in the examples hereof, were tested in accordance with at least one of the enzymatic and transactivation assays described hereinbelow and were found to have 17β-HSD3 inhibitory activity. The enzymatic activity of 17β-HSD3, as well as, the 17β-HSD3 inhibitory activity of various compounds within the scope of Formula I were determined either in cell extracts using a scintillation proximity assay (SPA), or within cells using a 17β-HSD3 driven secreted alkaline phosphatase (SEAP) reporter assay.

Scintillation Proximity Assay (SPA)

17β-HSD3 enzyme was prepared from HEK293 cells, which come from a human kidney epithelial cell line that does not express endogenous 17β-HSD3 protein but are engineered to over express a cDNA clone that encodes full length human 17β-HSD3. Stable clonal populations of 7β-HSD3 expressing HEK293 cells were established upon antibiotic selection with G418 (500 μg/ml). Individual 17β-HSD3 HEK293 transfectants were analyzed by Western blotting for 17β-HSD3 protein levels and assayed for androstenedione to testosterone conversion activity. Clonal populations with significant 17β-HSD3 activity were expanded and cellular lysates prepared for use in the 17β-HSD3 SPA via homogenization followed by high-speed centrifugation.

The inhibitory activity of at least one Formula I compound was first evaluated by using the 17β-HSD3 SPA format. Briefly, HEK293 lysates containing recombinant 17β-HSD3 were incubated with {3H} androstenedione for 60 minutes in a total volume of 30 μl while being gently rocked in either the presence, or absence of at least one Formula I compound (up to 30 μM). The enzymatic reaction of 17β-HSD3 was terminated by adding 10 μl of 0.1 N HCL. The {3H}-testosterone converted by 17β-HSD3 from androstenedione was captured and quantified using a monoclonal antibody against testosterone that was pre-conjugated to anti-mouse IgG Yttrium silicate SPA beads.

17β-HSD3 Driven Secreted Alkaline Phosphatase (SEAP) Reporter Assay

A 17β-HSD3-driven cell based assay was established using MB-MDA231 cells and an androgen-responsive gene promoter reporter construct. In this assay, the amount of testosterone converted by 17β-HSD3 from androstenedione was measured by monitoring the transcriptional activity of endogenous androgen receptors via androgen responsive prostate specific antigen (PSA) promoters.

To set up this system, MB-MDA231 cells, which do not express 17β-HSD3, were transfected with human 17β-HSD3 and clonal populations were selected and analyzed as described hereinabove in the SPA. The clonal cell lines were analyzed via thin layer chromatography (TLC) and those showing moderate androstenedione to testosterone conversion activity were used in determining the 17β-HSD3 inhibitory activity of at least one Formula I compound.

The 17β-HSD3-MB-MDA-231 transfectants were transfected with a PSA-SEAP reporter and grown in cell culture overnight. The PSA promoter contains several androgen receptor-binding elements which are sufficient to drive an androgen responsive transcriptional response. The following day, 17β-HSD3 transfectants containing the PSA-SEAP promoter were incubated with 10 nM androstenedione in either the presence, or absence of at least one Formula I compound for 18 hours. Cellular media was harvested and analyzed for alkaline phosphatase activity by standard methods.

A more detailed description of the assays utilized in testing the 17β-HSD3 inhibitory activity of at least one Formula I compound can be found in co-pending U.S. Patent Application Publication No 2005/0191707 A1, published Sep. 1, 2005, which is hereby incorporated herein by reference.

At least one Formula I compound showing 17β-HSD3 inhibitory activity in at least one of the above referenced assays had an $IC_{50}$ value of between about 0.01 to about 100 μM. In one embodiment, at least one Formula I compound showing 17β-HSD3 inhibitory activity in at least one of the above referenced assays had an $IC_{50}$ value less than about 1.0 μM. In another embodiment, at least one Formula I compound showing 17β-HSD3 inhibitory activity in at least one of the above referenced assays had an $IC_{50}$ value less than about 0.5 μM.

EXAMPLES

The present invention is further defined in the following Examples. It should be understood that these Examples are given by way of illustration only. From the above discussion and this Example, one skilled in the art can ascertain the essential characteristics of this invention, and without departing from the spirit and scope thereof, can make various changes and modifications to the invention to adapt the invention to various uses and conditions. As a result, the present invention is not limited by the illustrative examples set forth hereinbelow, but rather defined by the claims appended hereto.

Abbreviations

The following abbreviations are employed in the Examples set forth hereinbelow:

AcOH=acetic acid
BOP Reagent=Benzotriazol-1-yloxy-tris(dimethylamino)-phosphonium hexafluorophosphate
DCE=1,2-dichloroethane
DIC=diisopropylcarbodiimide
DMAP=N,N-dimethylamino pyridine
DMF=dimethylformamide
EDCI=1-[3-(Dimethylamino)propyl]-3-ethylcarbodiimide hydrochloride
EtOAc=ethyl acetate
EtOH=ethyl alcohol
HOAt=1-hydroxy-7-azabenztriazole
HOBt=1-hydroxybenzotriazole
MeOH=methanol
NMP=1-methyl-2-pyrrolidinone
NosCl=4-nitrobenzenesulfonyl chloride
TFA=trifluoroacetic acid; and THF=Tetrahydrofuran Example 1

2-[(3-chloro-4-hydroxybenzoyl)amino]-N-[2-(2-methoxyphenyl)ethyl]-5-phenoxybenzamide

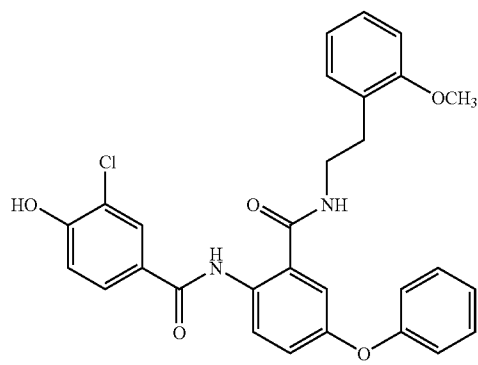

1A. Preparation of methyl 4-(3,4-dimethoxybenzyloxy)-3-chlorobenzoate

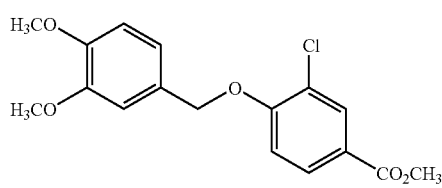

A solution of (3,4-dimethoxyphenyl)methanol (6.0 g, 40 mmol) (Aldrich Chemical Co., Milwaukee, Wis.) and methyl 3-chloro-4-hydroxybenzoate (2.5 g, 13.5 mmol) (Lancaster Synthesis Ltd, Windham, N.H.) in THF (100 mL) was cooled to 0° C. and treated with triphenylphosphine (8.8 g, 33.5 mmol). A solution of diethylazodicarboxylate (5.3 mL, 33.5 mmol) in THF (50 mL) was added dropwise over 30 minutes. After the addition was complete, the reaction was warmed to room temperature and stirred for an additional 30 minutes, and then concentrated to orange oil. The crude reaction was applied directly to a silica column and flushed with hexanes. The desired product was eluted from the column using 25% EtOAc in Hexanes to afford 1A as a light yellow solid (2.5 g, 56%).

1B. Preparation of 4-(3,4-Dimethoxybenzyloxy)-3-chlorobenzoic acid

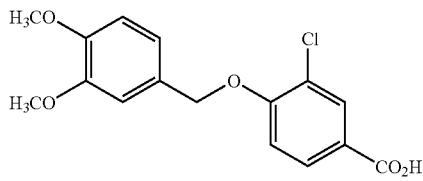

A solution of 1A (600 mg, 1.78 mmol) in THF (30 mL) and MeOH (10 mL) was treated with a solution of LiOH monohydrate (375 mg, 8.93 mmol) in water (10 mL) at room temperature. The resulting suspension was stirred at room temperature for 18 hours. The reaction was concentrated to 30 mL, diluted with water (50 mL) and cooled to 0° C. The solution was brought to pH 5 with 1 N HCl and the resulting solid was collected by vacuum filtration. Residual water was removed from the solid material using azeotrope with toluene to afford 1B as a white solid (370 mg, 65%).

1C. Preparation of ethyl 2-(4-(3,4-dimethoxybenzyloxy)-3-chlorobenzamido)-5-phenoxybenzoate

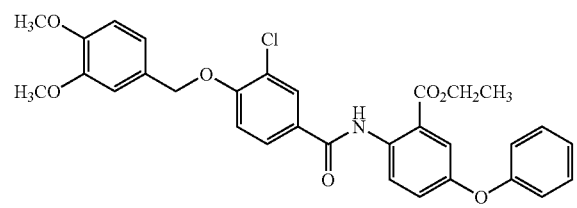

A solution of 1B (200 mg, 0.62 mmol) in $CH_2Cl_2$ (10 mL) was cooled to 0° C. and treated with several drops of DMF. Oxalyl chloride was added dropwise over 10 minutes. The resulting solution was stirred for 10 minutes, and then concentrated to dryness. The resulting solid was dissolved in $CH_2Cl_2$ (10 mL) and treated with ethyl 2-amino-5-phenoxybenzoate (144 mg, 0.56 mmol) and diisopropylethylamine (130 μL, 0.74 mmol). The reaction was stirred at room temperature for 3 hours and then concentrated to afford 1C as a white solid.

1D. Preparation of 2-(4-(3,4-dimethoxybenzyloxy)-3-chlorobenzamido)-5-phenoxybenzoic acid

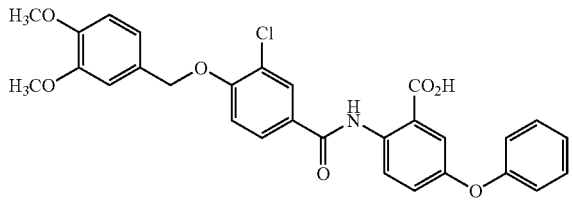

A solution of 1C (160 mg, 0.29 mmol) in THF (30 mL) and MeOH (10 mL) at 0° C. was treated with a solution of LiOH monohydrate (60 mg, 1.42 mmol) in water (10 mL). The resulting solution was stirred for 16 hours, and then concentrated to 10 mL. The resulting suspension was taken up in water (10 mL) and brought to pH 5 with 1 N HCl. The solution was extracted with EtOAc (4×25 mL), dried ($Na_2SO_4$), filtered and concentrated to afford the 1D as a white solid. (130 mg, 84%).

1E. Preparation of 2-[[3-chloro-4-[(3,4-dimethoxyphenyl)methoxy]benzoyl]amino]-N-[2-(2-methoxyphenyl)ethyl]-5-phenoxy-benzamide

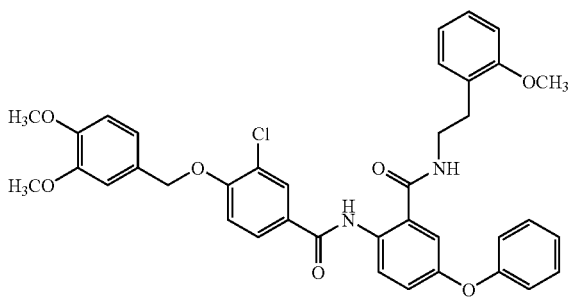

A solution of 1D (30 mg, 0.056 mmol) in DMF (2 mL) was treated with HOBt (15 mg, 0.11 mmol) and diisopropylcarbodiimide (13 μL, 0.084 mmol) at room temperature. The reaction was stirred for one hour then 2-methoxyphenethylamine was added. The resulting solution was stirred for three hours, concentrated and purified by chromatography ($SiO_2$, 0.5% MeOH in $CH_2Cl_2$) to afford 1E (27 mg, 73%).

1F. Preparation of 2-[(3-chloro-4-hydroxybenzoyl)amino]-N-[2-(2-methoxyphenyl)ethyl]-5-phenoxy-benzamide

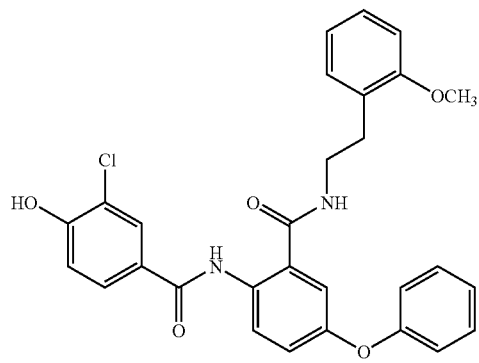

A solution of 1E (27 mg, 0.04 mmol) in $CH_2Cl_2$ (2 mL) at 0° C. was treated with TFA (100 μL). The reaction was warmed to room temperature and stirred for three hours. The mixture was poured into EtOAc:buffer (1:1, pH 7, 40 mL) and the layers were separated. The organic layer was washed with pH 7 buffer (1×10 mL), dried ($Na_2SO_4$), filtered and concentrated to a yellow oil. The crude product was purified by preparative HPLC to afford 1F as a white solid (19 mg, 88%). $^1$H NMR (Acetone-$d_6$) δ 8.80 (d, 1H, J=7.5 Hz), 8.17 (brs 1H), 8.01 (d, 1H, J=1.8 Hz), 7.81 (d, 1H, J=7.0 Hz), 7.45 (d, 1H, J=1.8 Hz), 7.36 (m, 2H), 7.15 (m, 5H), 6.97 (d, 1H, J=6.6 Hz), 6.89 (d, 1H, J=7.0 Hz), 6.79 (t, 1H, J=7.8 Hz), 3.77 (s, 3H), 3.64 (q, 2H, J=5.28 Hz), 2.93 (t, 2H, J=5.24 Hz). HPLC retention time=3.297 min. (YMC S5 ODS 4.6×50 mm, 10-90% aqueous methanol containing 0.2% $H_3PO_4$, 4 min gradient, monitored at 220 nm). m/z=516.9 (M+H$^+$).

Examples 2-8

Examples 2-8, which are set forth in Table 1 hereinbelow, were prepared in accordance with the procedure utilized in preparing Example 1.

TABLE 1

| Ex. No. | R¹ | R² | Compound Name | [M + H] | HPLC Ret Time (min)[a] |
|---|---|---|---|---|---|
| 2 | 2-methoxyphenethyl (OMe) | H | 3-chloro-4-hydroxy-N-[2-({[2-(2-methoxyphenyl)ethyl]amino}carbonyl)phenyl]benzamide | 425 | 3.58 |
| 3 | isobutyl | —OPh | 2-[(3-chloro-4-hydroxybenzoyl)amino]-N-ethyl-5-phenoxybenzamide | 366 | 2.59 |
| 4 | 2-chlorophenethyl (Cl) | —OPh | 2-[(3-chloro-4-hydroxybenzoyl)amino]-N-[2-(2-chlorophenyl)ethyl]-5-phenoxybenzamide | 521 | 3.41 |
| 5 | isobutyl | H | 3-chloro-N-{2-[(ethylamino)carbonyl]phenyl}-4-hydroxybenzamide | NA | 3.04 |
| 6 | phenethyl | H | 3-chloro-4-hydroxy-N-(2-{[(2-phenylethyl)amino]carbonyl}phenyl)benzamide | 395 | 3.51 |
| 7 | 2-chlorophenethyl (Cl) | H | 3-chloro-N-[2-({[2-(2-chlorophenyl)ethyl]amino}carbonyl)phenyl]-4-hydroxybenzamide | 429 | 3.66 |
| 8 | phenethyl | —OPh | 2-[(3-chloro-4-hydroxybenzoyl)amino]-5-phenoxy-N-(2-phenylethyl)benzamide | 487 | 3.22 |

[a] HPLC Conditions: YMC S5 ODS 4.6 × 50 mm, 10-90% aqueous methanol containing 0.2% $H_3PO_4$, 4 min gradient, monitored at 220 nm).

Example 9

Preparation of Formula 9G compounds

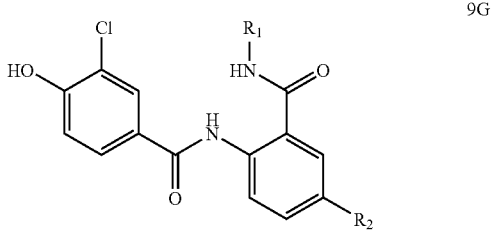

9G wherein $R_1$ is selected from the various $R_1$ groups identified in Tables 2 and 3; and $R_2$=OMe, OPh, or H.

Example 9 is directed to the general library synthesis procedure that was utilized in preparing Examples 10-33, which are set forth in Tables 2 and 3 hereinbelow.

IRORI MicroKans™, which can be purchased from Discovery Partners Int. (San Diego, Calif.), are made of high-grade polypropylene with polypropylene mesh in the sidewalls and cap. Each MicroKan™ is loaded with a unique radiofrequency tag (RF tag) that is used to track the synthesis sequence for each MicroKan™. Each MicroKan™ is also loaded with resin beads. The synthesis sequence is carried out on the resin beads. Each MicroKan™ has a volume of 250 uL and can hold up to 31 mg of resin. The mesh sides and lid of the MicroKan™ allow reagents and solvents to interact with the resin inside the MicroKan™. Prior to each synthesis step with a new building block reagent (e.g. anthranilic ester), the RF tag in each MicroKan™ is read. Following the reading, the MicroKan™ is sorted to the appropriate reservoir for the next reaction using IRORI Synthesis Manager software. At the end of the synthesis sequence, the IRORI Synthesis Manager is able, based on the RF tag identifier, to identify the structure that has been prepared on the resin contained in each MicroKan™.

Mettler Toledo MiniBlocks, manufactured by Mettler Toledo, (Columbus, Ohio) are a parallel synthesis tool that can be used for solution-phase and solid-phase chemistry. For the synthesis procedure described below, 48 well MiniBlocks fitted with fritted 4 mL polypropylene tubes were used. The MiniBlocks were used for the cleavage of products prepared using IRORI MicroKans™. The MicroKans™ were sorted into the MiniBlock using the IRORI Synthesis Manager software, and a cleavage cocktail was added to the MicroKan™. The 48 tubes were drained into 48 wells of a 96 well plate using a vacuum collection manifold commercially available from Mettler Toledo.

9A. Preparation of p-Benzyloxybenzyl chloride resin (Pol-CH$_2$—Cl)

To triphenylphosphine (6.3 g, 24 mmol) in anhydrous CH$_2$Cl$_2$ (50 mL) cooled to 0° C. was slowly added triphosgene (7.13 g, 24 mmol) in anhydrous CH$_2$Cl$_2$ (25 mL). Significant gas evolution occurred during addition of the triphosgene. The reaction was stirred for 15 minutes at 0° C. and then the solvents were removed under vacuum. The resulting white residue was dissolved in CH$_2$Cl$_2$ (50 mL) and added to a pre-swollen suspension of p-benzyloxybenzyl alcohol polystyrene resin, (Argonaut Technologies Inc., (acquired by Biotage, Uppsala, Sweden)) (5 g, 1.21 mmol/g) in CH$_2$Cl$_2$. The slurry was shaken overnight on a wrist action shaker. The solvent was removed by vacuum filtration, and the resin was washed with CH$_2$Cl$_2$ (3×), THF (3×), and ether (3×), followed by drying under vacuum.

9B. Preparation of methyl 4-(4-(benzyloxy polystyrene)benzyloxy)-3-chlorobenzoate resin

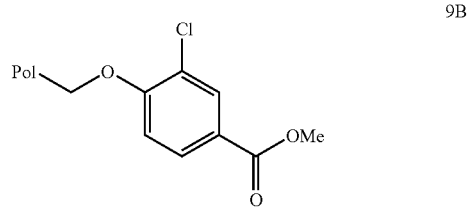

9B

To a suspension of NaH (1.8 g, 45 mmol) in DMF (120 mL) cooled to 0° C. was slowly added methyl 3-chloro-4-hydroxybenzoate (8.4 g, 45 mmol) in DMF (100 mL). Ten minutes after addition of the phenol the reaction vessel was warmed to room temperature. The solution was stirred for an additional 30 minutes, and then catalytic tetrabutylammonium iodide (50 mg) was added, followed by the addition of 9A p-benzyloxybenzyl chloride resin (25 g, 1.2 mmol/g). The reaction vessel was placed on an orbital shaker and heated to 70° C. overnight. After cooling to room temperature, the resin was washed with DMF (3×), THF (3×) and CH$_2$Cl$_2$ (3×), followed by drying under vacuum to afford 9B.

After determining the phenol loading level as described below, the remaining resin was used directly in step 9C. The loading level of resin 9B was determined by treating 103 mg of resin with 10% TFA in DCE for 1.5 hours, followed by filtration, and concentration of the solution. The loading level was determined to be 1.0 mmol/g based on the mass of the cleaved phenol.

9C. Preparation of 4-(4-(benzyloxy polystyrene) benzyloxy)-3-chlorobenzoic acid resin

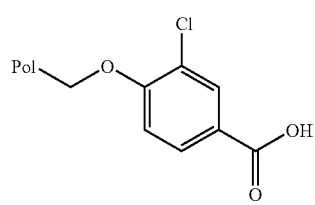

9C

A solution of potassium trimethylsilanolate (16.1 g, 125 mmol) in THF (200 mL) was filtered to remove a cloudy white film. The filtered solution was added to resin 9B (1 mmol/g) in a round bottom flask, and the flask was placed on an orbital shaker overnight. The resin was washed with THF (2×), 8:1:1 THF/AcOH/H$_2$O (2×), THF (2×), and CH$_2$Cl$_2$ (3×). The resin was air dried followed by drying under vacuum to afford 16 g of resin 9C.

9D. Preparation of Formula 9D compounds

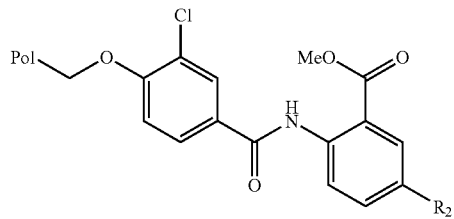

9D wherein $R_2$=OMe, OPh, or H.

Irori MicroKans™ containing RF tags were filled with resin 9C (30 mg/MicroKan™). The MicroKans™ were sorted using the IRORI Synthesis Manager according to reaction with the appropriate anthranilic ester. Two amide coupling procedures (Procedures A and B) were utilized in performing the anthranilic ester coupling step. The particular procedure chosen and compounds produced depended on the anthranilic ester used in the coupling step.

Procedure A. Preparation of methyl 2-(4-(4-(benzyloxy polystyrene)benzyloxy)-3-chlorobenzamido)-5-methoxybenzoate resin

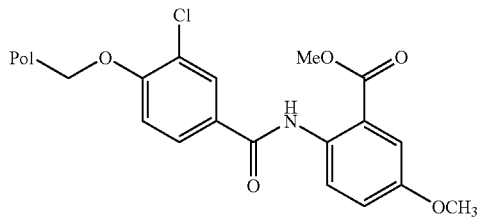

9D-1 wherein anthranilic ester=methyl 2-amino-5-methoxybenzoate and $R_2$=OMe.

The MicroKans™ were washed once with DCE prior to addition of reagents. A solution of 1,3-diisopropylcarbodiimide (0.1 M) and 1-hydroxy-7-azabenzotriazole (0.2 M) in NMP (0.75 mL/MicroKan™) was prepared. The solution was added to the MicroKans™ in a round bottom flask, and the mixture was degassed. The round bottom flask was put on a shaker for two hours. Then methyl 2-amino-5-methoxybenzoate (0.4 M) was added. The flask was heated to 70° C. for 48 hours, and the MicroKans™ were washed with DMF (3×), 8:1:1 THF/H$_2$O/AcOH (2×), and THF (3×) to afford 9D-1.

Procedure B. Preparing 9D-2 and 9D-3

9D-2. Preparation of methyl 2-(4-(4-(benzyloxy polystyrene)benzyloxy)-3-chlorobenzamido)-5-phenoxybenzoate resin

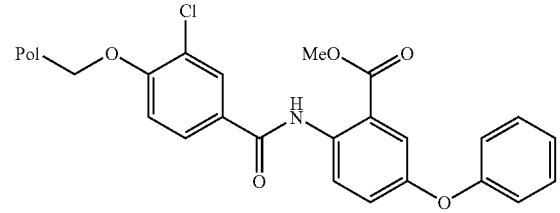

9D-2 wherein anthranilic ester=methyl 2-amino-5-phenoxybenzoate and $R_2$=OPh.

9D-3. Preparation of methyl 2-(4-(4-(benzyloxy polystyrene)benzyloxy)-3-chlorobenzamido)benzoate resin

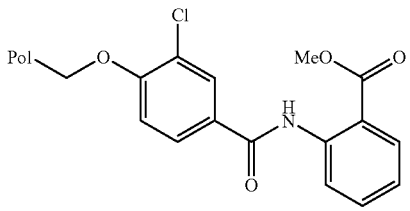

9D-3 wherein anthranilic ester=methyl 2-aminobenzoate and $R_2$=H.

The MicroKans™ were washed once with DCE prior to addition of reagents. A solution of 4-nitrobenzenesulfonyl chloride (0.07 M) and diisopropylethylamine (0.1 M) in 1,2-dichlorobenzene (0.75 mL/MicroKan™) was prepared. The solution was added to the appropriate MicroKans™ in a round bottom flask, and the mixture was degassed. The round bottom flask was put on an orbital shaker for two hours. Then methyl 2-amino-5-phenoxybenzoate (0.18 M), or methyl 2-aminobenzoate (0.21 M) was added to the flask. The reaction flask was heated to 70° C. for 36 hours on an orbital shaker. After washing with DCE (1×), DMF/DCE (3×), CH$_2$Cl$_2$ (3×), and DCE (1×) the coupling procedure was repeated. Finally, the MicroKans™ were washed with DMF (3×), 8:1:1 THF/H$_2$O/AcOH (2×), and THF (3×) to afford 9D-2 and/or 9D-3.

9E. Preparation of Formula 9E compounds

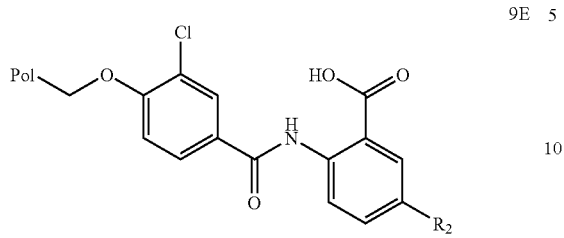

9E wherein $R_2$=OMe, OPh, or H.

A solution of potassium trimethylsilanolate (0.15 M) in THF (0.875 mL/MicroKan™) was filtered to remove a white cloudy substance. The filtered solution was then added to the 9D MicroKans™ of Procedure A or B in a reservoir. The mixture was degassed and shaken overnight on an orbital shaker. The solution was removed and the MicroKans™ were washed with 8:1:1 THF/H$_2$O/AcOH (2×), THF (3×), and CH$_2$Cl$_2$ (3×), and dried under vacuum to afford a compound in accordance with Formula 9E, wherein $R_2$=OMe, OPh, or H.

9F. Preparation of Formula 9F compounds

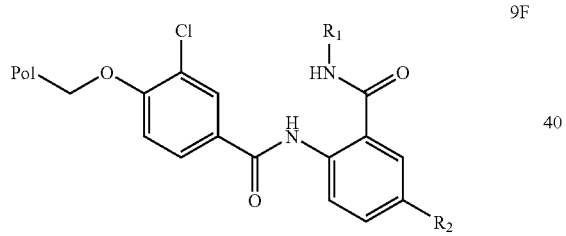

9F wherein $R_1$ is selected from the various $R_1$ groups identified in Tables 2 and 3; and $R_2$=OMe, OPh, or H.

The 9E MicroKans™ were sorted prior the coupling of $R_1$—NH. A solution of 1,3-diisopropylcarbodiimide (0.1 M) and 1-hydroxy-7-azabenzotriazole (0.2 M) in NMP (0.87 mL/MicroKans™) was prepared and added to the 9E MicroKans™ in a reservoir. The mixture was degassed and placed on an orbital shaker for 1.5 hours. The appropriate $R_1$—NH (0.4 M) was then added to the mixture, and the reservoir was heated to 50-60° C. overnight. The solvent was removed, the MicroKans™ washed with NMP (2×), and the resin again subjected to the amide coupling reagents described above. The MicroKans™ were washed with NMP (1×), DMF (2×), 8:1:1 THF/H$_2$O/AcOH (2×), THF (2×) and CH$_2$Cl$_2$ (2×), and dried under vacuum to afford compound in accordance with formula 9F, wherein $R_1$ is selected from the various $R_1$ groups identified in Tables 2 and 3; and $R_2$=OMe, OPh, or H.

9G. Preparation of Formula 9G compounds

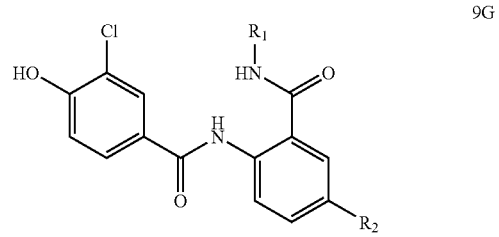

9G wherein $R_1$ is selected from the various $R_1$ groups identified in Tables 2 and 3; and $R_2$=OMe, OPh, or H The 9F MicroKans™ were sorted individually into Mettler Toledo MiniBlocks™ for the cleavage reactions. To each fritted polypropylene tube containing a MicroKan™ was added a 1 mL solution of 10% TFA in DCE. The MiniBlock™ was placed on an orbital shaker for 1 hour. The solvent was subsequently drained into a 96 deep well plate, and an additional 0.8 mL of 10% TFA in DCE was added to the fritted polypropylene tube containing the MicroKan™. The MiniBlock™ was placed on an orbital shaker for 1 hour. The solvent was again collected into the 96 deep well plate. The solvent was evaporated in a SAVANT Speedvac Plus under vacuum. After concentration, 1 mL of MeOH was added to each well followed by evaporation. A second addition of 1 mL of MeOH followed by concentration afforded the Example 10-25 compounds listed in Table 2. The product purity and identity were determined by HPLC and mass spectra analysis. Compounds that were determined to be >70% pure by HPLC and had the correct M+H or M−H were not further purified.

HPLC Method: Gradient elution 30-100% B/A over 2 minutes (solvent A=10% MeOH/H$_2$O containing 0.1% TFA, solvent B=90% MeOH/H$_2$O containing 0.1% TFA), flow rate 5 mL/min, UV detection at 250 nm. HPLC columns: Column A: YMC ODS S5 (4.6×33 mm); Column B: YMC ODS S3 (4.6×33 mm); Column C: Phenom-Prime S5 (4.6×30 mm); Column D: Phenomenex S5 ODS (4.6×30 mm).

Purification Method. Example 10-29 compounds having a purity of ≦70% were further purified in accordance with the following method. The Examples that required further purification are identified in Tables 2 and 3 via an asterisk (*) that has been placed next to each HPLC retention time associated with those further purified compounds.

The Example 10-29 compounds having a purity of ≦70% were found to be contaminated with a significant amount of benzo[d][1,3]oxazin-4-one impurity. As a result, such compounds were subjected to resin scavenging using Supelco Diaion® WA21J polyamine resin (Sigma-Aldrich, St. Louis, Mo.), which, prior to being used, was soaked overnight in 1:1 DCE/ethanol at 40-50° C. and then washed with DMF (2×), THF (2×) and CH$_2$Cl$_2$ (3×). Each compound having a purity of ≦70% was separately dissolved in 0.85 mL of 1:1 DCE/ethanol, and transferred to a MiniBlock™ reservoir. 50 mgs of pretreated WA21J resin was subsequently added to each reservoir. The MiniBlock™ was sealed, placed on an orbital shaker and heated to 50° C. for 18-24 h. The solvent was collected in a 96 deep well plate, and the resin was washed with 1:1 DCE/ethanol (2×0.4 mL). The solvents were evaporated using a SAVANT Speedvac Plus. The product purity and identity were determined via the HPLC and mass spectra analysis already described hereinabove.

Examples 10-25

Examples 10-25, which are set forth in Table 2 hereinbelow, were prepared in accordance with the procedure set forth in Example 9.

TABLE 2

| Ex. No. | R¹ | R² | Compound Name | [M + H] | [M − H] | HPLC Ret Time (min) | HPLC Column |
|---|---|---|---|---|---|---|---|
| 10 | phenethyl | —OPh | 2-[(3-chloro-4-hydroxybenzoyl)amino]-5-phenoxy-N-(2-phenylethyl)benzamide | 487.1 | | 1.85 | A |
| 11 | isopropyl | —OMe | 2-[(3-chloro-4-hydroxybenzoyl)amino]-N-isopropyl-5-methoxybenzamide | | 361.1 | 1.33* | A |
| 12 | isobutyl | —OPh | 2-[(3-chloro-4-hydroxybenzoyl)amino]-N-isobutyl-5-phenoxybenzamide | | 437.0 | 1.92 | B |
| 13 | 2-(4-methoxyphenyl)ethyl | —OPh | 2-[(3-chloro-4-hydroxybenzoyl)amino]-N-[2-(4-methoxyphenyl)ethyl]-5-phenoxybenzamide | | 515.2 | 1.96 | B |
| 14 | 2-(3-methoxyphenyl)ethyl | —OPh | 2-[(3-chloro-4-hydroxybenzoyl)amino]-N-[2-(3-methoxyphenyl)ethyl]-5-phenoxybenzamide | | 515.2 | 1.93 | B |
| 15 | 2-(3-methoxyphenyl)ethyl | H | 3-chloro-4-hydroxy-N-[2-({[2-(3-methoxyphenyl)ethyl]amino}carbonyl)phenyl]benzamide | | 423.1 | 1.59 | B |
| 16 | 2-(4-methoxyphenyl)ethyl | H | 3-chloro-4-hydroxy-N-[2-({[2-(4-methoxyphenyl)ethyl]amino}carbonyl)phenyl]benzamide | | 423.1 | 1.59 | A |

TABLE 2-continued

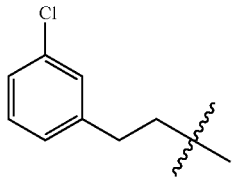

| Ex. No. | R¹ | R² | Compound Name | [M + H] | [M − H] | HPLC Ret Time (min) | HPLC Column |
|---|---|---|---|---|---|---|---|
| 17 | 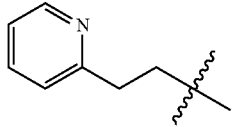 | H | 3-chloro-N-[2-({[2-(3-chlorophenyl)ethyl]amino}carbonyl)phenyl]-4-hydroxybenzamide | | 427.1 | 1.75 | A |
| 18 | 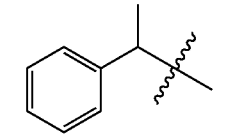 | —OPh | 2-[(3-chloro-4-hydroxybenzoyl)amino]-5-phenoxy-N-(2-pyridin-2-ylethyl)benzamide | | 486.2 | 1.39 | A |
| 19 | 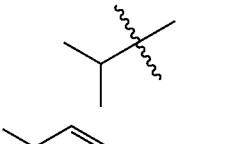 | —OPh | 2-[(3-chloro-4-hydroxybenzoyl)amino]-5-phenoxy-N-(1-phenylethyl)benzamide | | 485.2 | 1.94 | A |
| 20 | 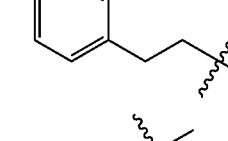 | —OPh | 2-[(3-chloro-4-hydroxybenzoyl)amino]-N-isopropyl-5-phenoxybenzamide | | 423.1 | 1.81 | A |
| 21 | 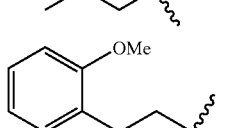 | —OPh | 2-[(3-chloro-4-hydroxybenzoyl)amino]-N-[2-(4-chlorophenyl)ethyl]-5-phenoxybenzamide | | 519.2 | 2.08 | A |
| 22 |  | —OPh | 2-[(3-chloro-4-hydroxybenzoyl)amino]-5-phenoxy-N-propylbenzamide | | 423.1 | 1.83 | A |
| 23 | 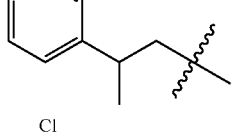 | —OMe | 2-[(3-chloro-4-hydroxybenzoyl)amino]-5-methoxy-N-[2-(2-methoxyphenyl)ethyl]benzamide | | 453.3 | 1.53 | A |
| 24 | 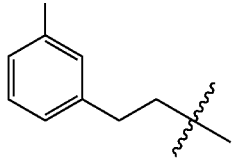 | —OPh | 2-[(3-chloro-4-hydroxybenzoyl)amino]-5-phenoxy-N-(2-phenylpropyl)benzamide | 501.2 | | 1.89 | A |
| 25 |  | —OPh | 2-[(3-chloro-4-hydroxybenzoyl)amino]-N-[2-(3-chlorophenyl)ethyl]-5-phenoxybenzamide | | 519.1 | 2.04 | B |

*The compound was purified using Supelco Diaion ® WA21J scavenging resin as described in 9G.

Examples 26-29

Examples 26-29, which are set forth in Table 3 hereinbelow, were prepared in accordance with the procedure set forth in Example 9. The resin 9B loading level utilized in preparing the Table 3 compounds ranged from 0.36 mmol/g to 1.0 mmol/g depending on the phenol loaded.

TABLE 3

| Ex. No. | R¹ | (R₃)ₙ group | Compound Name | [M + H] | [M − H] | HPLC Ret Time (min) | HPLC Column |
|---|---|---|---|---|---|---|---|
| 26 | isopropyl | 4-hydroxy-3-methylphenyl | 2-[(4-hydroxy-3-methylbenzoyl)amino]-N-isopropyl-5-phenoxybenzamide | 405.2 | | 1.78 | A |
| 27 | 2-(2-chlorophenyl)ethyl | 4-hydroxyphenyl | N-[2-(2-chlorophenyl)ethyl]-2-[(4-hydroxybenzoyl)amino]-5-phenoxybenzamide | 485.2 | | 1.76* | A |
| 28 | isopropyl | 4-hydroxyphenyl | 2-[(4-hydroxybenzoyl)amino]-N-isopropyl-5-phenoxybenzamide | 389.2 | | 1.50 | A |
| 29 | 2-(4-chlorophenyl)ethyl | 3-hydroxyphenyl | N-[2-(4-chlorophenyl)ethyl]-2-[(3-hydroxybenzoyl)amino]-5-phenoxybenzamide | 485.2 | | 1.96 | A |

*The compound was purified using Supelco Diaion ® WA21J scavenging resin as described in 9G.

Example 30

2-[(3-chloro-4-hydroxybenzoyl)amino]-4,5-dimethoxy-N-[2-(2-methoxyphenyl)ethyl]benzamide

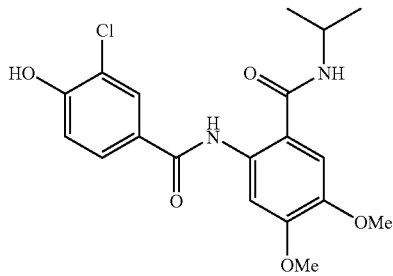

Example 30 was prepared in accordance with the procedure set forth in Example 9, wherein anthranilic ester=methyl 2-amino-4,5-dimethoxybenzoate and Procedure A as described in 9D was utilized. The resulting compound was purified via WA21J scavenging resin in accordance with the Purification Method described in 9G. HPLC retention time=1.70 min (Column A). m/z=483.2 (M−H).

Example 31

3-[(2-hydroxy-5-methylbenzoyl)amino]-N-1,2,3,4-tetrahydronaphthalen-1-yl-2-naphthamide

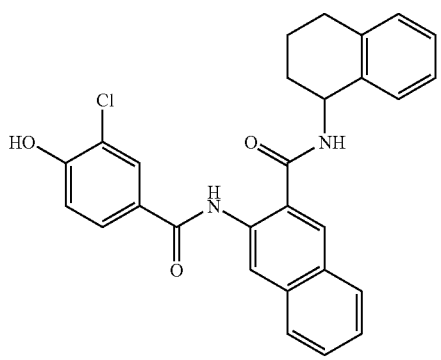

Example 31 was prepared in accordance with the procedure set forth in Example 9, wherein anthranilic ester=methyl 3-amino-2-naphthoate and Procedure B as described in 9D was utilized. HPLC retention time=2.23 min (Column A). m/z=449.3 (M−H).

Example 32

3-[(3-chloro-4-hydroxybenzoyl)amino]-N-isopropyl-2-naphthamide

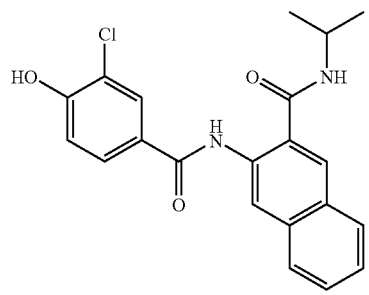

Example 32 was prepared in accordance with the procedure set forth in Example 9, wherein anthranilic ester=methyl 3-amino-2-naphthoate and Procedure B as described in 9D was utilized. HPLC retention time=1.62 min (Column D). m/z=381.1 (M−H).

Example 33

2-[(3-chloro-4-hydroxybenzoyl)amino]-N-[2-(2-methoxyphenyl)ethyl]-4-methylbenzamide

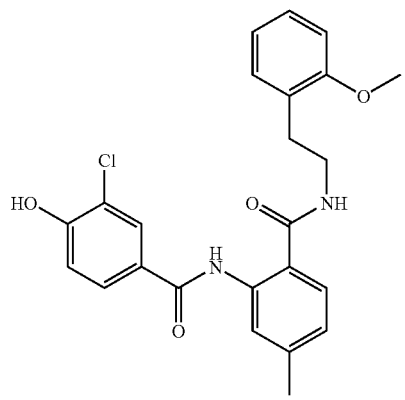

Example 33 was prepared in accordance with the procedure set forth in Example 9, wherein anthranilic ester=methyl 2-amino-4-methylbenzoate was performed using Procedure B described in 9D. HPLC retention time=1.67 min (Column C). m/z=437.2 (M−H).

Example 34

4-[({2-[(isopropylamino)carbonyl]-4-phenoxyphenyl}amino)carbonyl]benzoic acid

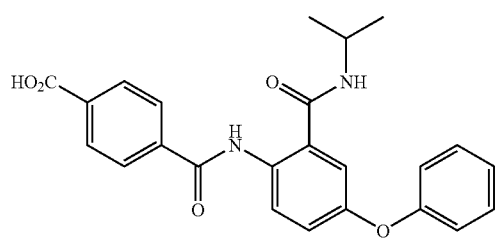

34A. Preparation of 2-nitro-5-phenoxybenzoic acid

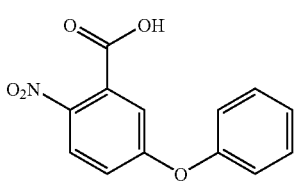

A solution of 5-fluor-2-nitrobenzoic acid (2.6 g, 14.1 mmol, Aldrich Chemical Co., Milwaukee, Wis.) and phenol (1.5 g, 15.5 mmol, Aldrich Chemical Co., Milwaukee, Wis.) in DMF (70 mL) was treated with $K_2CO_3$ (5.9 g, 42.4 mmol) and heated to 120° C. for 6 hours. The reaction was cooled to room temperature and the solvent removed under reduced pressure. The resulting residue was dissolved in water and extracted with EtOAc. The combined organic layers were washed with saturated aqueous NaCl, dried ($Na_2SO_4$), filtered, and concentrated to afford 34A (4.5 g).

34B. Preparation of 2-nitro-N-isopropyl-5-phenoxybenzamide

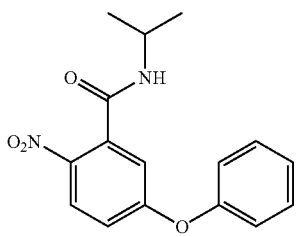

A solution of 34A (1.0 g, 3.86 mmol) in $CH_2Cl_2$ (15 mL) was treated with one drop of DMF. Oxalyl chloride (2.2 mL, 2M in $CH_2Cl_2$, 4.4 mmol) was added dropwise at room temperature. The reaction mixture was stirred for 1 hour, and then concentrated to dryness. The crude acid chloride was dissolved in $CH_2Cl_2$ and cooled to 0° C. Diisopropylamine (600 mg, 10 mmol) in $CH_2Cl_2$ (2 mL) was added slowly and the resulting mixture was stirred for one hour at room temperature. The reaction was concentrated and partitioned between EtOAc (20 mL) and 1M HCl (20 mL). The organic layer was washed with 1 M HCl (20 mL), saturated aqueous $NaHCO_3$ (20 mL), and brine (20 mL). The organic layer was dried ($Na_2SO_4$), filtered, and concentrated to a brown solid. The crude amide was recrystallized from EtOAc/heptane to afford 34B (740 mg, 64%).

34C. Preparation of 2-amino-N-isopropyl-5-phenoxybenzamide

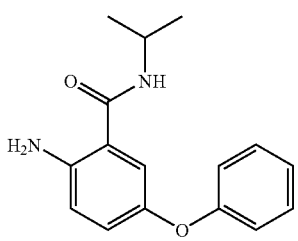

A solution of 34B (710 mg, 2.37 mmol) in MeOH (8 mL) was treated with 20% palladium hydroxide on carbon (110 mg). The resulting slurry was stirred under a hydrogen atmosphere for 4 hours, and then filtered through a 0.4 μm polycarbonate membrane to remove the catalyst. The filtrate was concentrated to give 34C as a white solid (636 mg, 99%).

34D. Preparation of methyl 4-((2-(isopropylcarbamoyl)-4-phenoxyphenyl)carbamoyl)benzoate

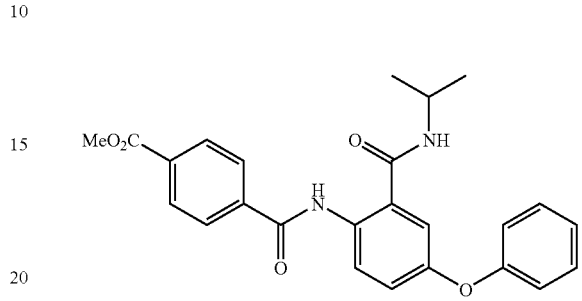

A solution of 34C (72 mg, 0.27 mmol) in DMF (4 mL) was treated with 4-(methoxycarbonyl)benzoic acid (78 mg, 0.43 mmol), HOBt (66 mg, 0.43 mmol) and triethylamine (100 mg, 1.0 mmol). The solution was treated with EDCI (96 mg, 0.5 mmol) at room temperature for 15 minutes, and then warmed to 65° C. for 16 hours. The reaction mixture was partitioned between EtOAc (20 mL) and 1 M HCl (20 mL). The organic layer was washed with 1 N HCl (20 mL), 1 N NaOH (20 mL) and brine (20 mL). The reaction was dried ($Na_2SO_4$), filtered, and concentrated to a solid. The crude material was purified by chromatography ($SiO_2$, 1:2 EtOAc in heptane) to afford 34D (99 mg, 85%).

34E. Preparation of 4-((2-(isopropylcarbamoyl)-4-phenoxyphenyl)carbamoyl)benzoic acid

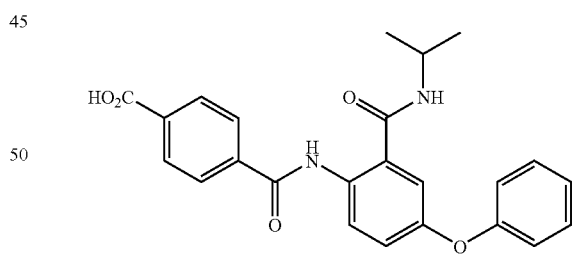

A solution of 34D (80 mg, 0.19 mmol) in THF (2 mL) was treated with 1 N NaOH (0.4 mL). The resulting solution was stirred for 20 hours. The reaction mixture was treated with 1 N HCl (0.6 mL) and partitioned between EtOAc (20 mL) and water (20 mL). The organic layer was washed with brine (20 mL), dried ($Na_2SO_4$), and concentrated to afford 34E (75 mg, 94%). HPLC retention time: 4.34 minutes (YMC S-5 ODS-A 4.6×50 mm, 10% to 90% MeOH/$H_2O$ w/0.2% $H_3PO_4$, 4 minute gradient).

Examples 35-41

Examples 35-41, which are set forth in Table 4 hereinbelow, were prepared from the appropriate starting materials in accordance with the procedure utilized in preparing Example 34.

TABLE 4

| Ex. No. | (R₃)ₙ group | Compound Name | [M + H] | HPLC Ret Time (min)ᵃ |
|---|---|---|---|---|
| 35 | 3-HO₂C-phenyl | 3-[({2-[(isopropylamino)carbonyl]-4-phenoxyphenyl}amino)carbonyl]benzoic acid | 419 | 4.28 |
| 36 | 4-MeO₂SHN-phenyl | N-isopropyl-2-({4-[(methylsulfonyl)amino]benzoyl}amino)-5-phenoxybenzamide | NA | 4.11 |
| 37 | 3-chloro-4-hydroxy-5-methylphenyl | 3-chloro-4-hydroxy-N-{2-[(isopropylamino)carbonyl]-4-phenoxyphenyl}-5-methylbenzamide | 461 [M + Na]+ | 4.52 |
| 38 | 4-HS-phenyl | N-isopropyl-2-[(4-mercaptobenzoyl)amino]-5-phenoxybenzamide | 405 [M − H]− | 4.51 |
| 39 | 3,5-dichloro-4-hydroxyphenyl | 3,5-dichloro-4-hydroxy-N-{2-[(isopropylamino)carbonyl]-4-phenoxyphenyl}benzamide | 459 | 4.57 |
| 40 | 1H-indol-5-yl | N-{2-[(isopropylamino)carbonyl]-4-phenoxyphenyl}-1H-indole-5-carboxamide | 412 [M − H]− | 4.27 |

TABLE 4-continued

| Ex. No. | | Compound Name | [M + H] | HPLC Ret Time (min)[a] |
|---|---|---|---|---|
| 41 | 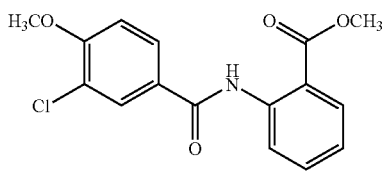 | 2-[(3-chlorobenzoyl)amino]-N-isopropyl-5-phenoxybenzamide | NA | 4.70 |

[a] YMC S5 ODS column 4.6 × 50 mm, 10-90% aqueous methanol over 4 minutes containing 0.2% phosphoric acid, 4 mL/min, monitoring at 220 nm

Example 42

3-chloro-4-methoxy-N-(2-{[(2-phenylethyl)amino]carbonyl}phenyl)benzamide

42A. Preparation of methyl 2-(3-chloro-4-methoxybenzamido)benzoate

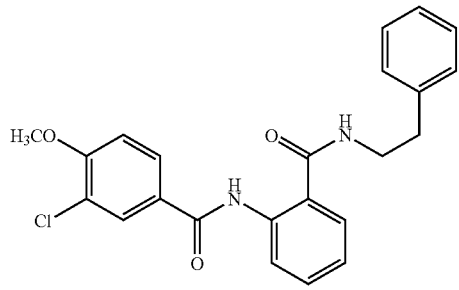

A solution of methyl 2-aminobenzoate (500 mg, 3.3 mmol) (Aldrich Chemical Co., Milwaukee, Wis.) and 3-chloro-4-methoxybenzoic acid (645 mg, 3.3 mmol) (Lancaster Synthesis Ltd., Windham, N.H.) in DMF (20 mL) was treated with EDCI (1.3 g, 6.6 mmol) and DMAP (800 mg, 6.6 mmol) at room temperature. The reaction mixture was stirred for 24 hours, and then concentrated. The crude residue was dissolved in EtOAc (50 mL) and washed with 0.1 N HCl (2×20 mL), saturated aqueous NaHCO$_3$ (2×20 mL). The organic layer was dried (Na$_2$SO$_4$), filtered, and concentrated. The crude product was purified by chromatography (SiO$_2$, 15% EtOAc in hexanes) to afford 42A as a white solid (350 mg, 33%).

42B. Preparation of 2-(3-chloro-4-methoxybenzamido)benzoic acid

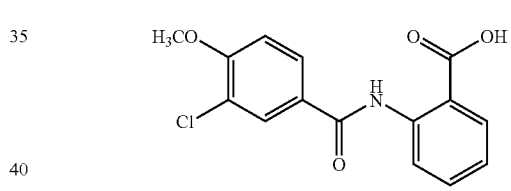

A solution of 42A (340 mg, 1.1 mmol) in THF (30 mL)/MeOH (10 mL) was treated with a solution of LiOH monohydrate (223 mg, 5.3 mmol) in water (10 mL). The reaction was stirred for 24 hours at room temperature and concentrated to a yellow solid. The crude acid was dissolved in water (100 mL) and acidified with 1 N HCl to pH 4. The resulting solid was collected by vacuum filtration and washed with water (2×100 mL) to afford 42B (260 mg, 85%).

42C. Preparation of 3-chloro-4-methoxy-N-(2-{[(2-phenylethyl)amino]carbonyl}phenyl)benzamide

42C

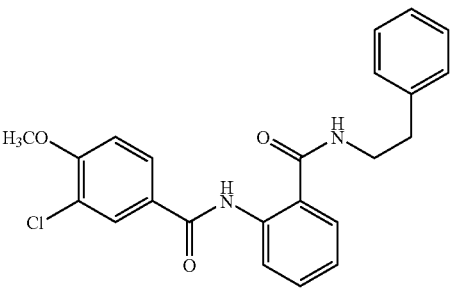

A solution of 42B (50 mg, 0.16 mmol) in DMF (5 mL) was treated with phenethylamine (150 μL, 1.6 mmol), diisopropylethylamine (42 mL, 0.32 mmol), and EDCI (31 mg, 0.32 mmol) at room temperature. After 2 hours Bop reagent (100 mg, 0.22 mmol) was added. After 30 minutes, the reaction was concentrated and purified by chromatography (SiO$_2$, 30% EtOAc in hexanes) to afford 42C (47 mg, 70%). HPLC retention time: 2.79 minutes (YMC S-5 Combiscreen 4.6×50 mm, 10% to 90% MeOH/H$_2$O w/0.2% H$_3$PO$_4$, 4 minute gradient).

Example 43

2-[(3-chloro-4-methoxybenzoyl)amino]-5-phenoxy-N-(2-phenylethyl)benzamide

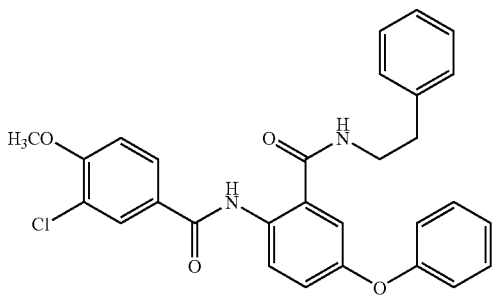

43A. Preparation of ethyl 2-nitro-5-phenoxybenzoate

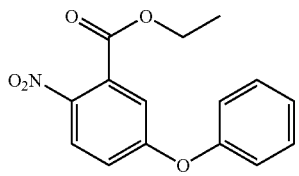

A solution of 34A (4.5 g, 17.4 mmol) in EtOH (120 mL) was treated with concentrated H$_2$SO$_4$ (4 mL) and heated to reflux for 24 hours. The mixture was cooled to room temperature and neutralized with 5% NaHCO$_3$. The resulting solution was extracted with CH$_2$Cl$_2$, dried (MgSO$_4$), filtered, and concentrated to afford 43A (2.6 g, 65%).

43B. Preparation of ethyl 2-amino-5-phenoxybenzoate

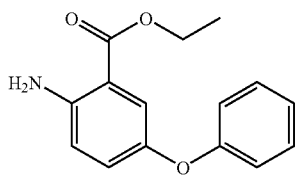

A solution of 43A (3.35 g, 11.7 mmol) in MeOH (30 mL):EtOAc (30 mL) was degassed with argon for 30 minutes. The resulting solution was treated with 10% Pd/C (335 mg) and stirred under a hydrogen atmosphere for 2 hours. The reaction mixture was filtered through a pad of celite and concentrated to afford 43B (2.6 g, 87%).

43C. Preparation of ethyl 2-(3-chloro-4-methoxybenzamido)-5-phenoxybenzoate

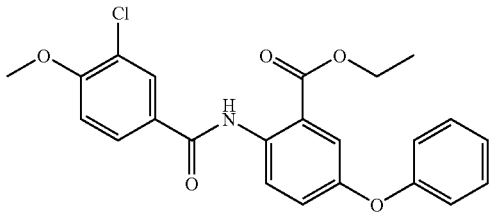

A solution of 3-chloro-4-methoxy benzoic acid (Lancaster Synthesis Ltd., Windham, N.H.) (100 mg, 0.54 mmol) in CH$_2$Cl$_2$ (5 mL) was cooled to −40° C. DMF (one drop) was added followed by oxalyl chloride (0.32 mL, 0.64 mmol, and 2M solution in CH$_2$Cl$_2$). The reaction was warmed to room temperature and stirred for 1 hour. The mixture was then concentrated to dryness and dried under high vacuum for several hours. The crude acid chloride (38 mg, 0.18 mmol) was dissolved in CH$_2$Cl$_2$ (2 mL) and treated with a solution of 43B (48 mg, 0.18 mmol) in CH$_2$Cl$_2$ (2 mL). Triethylamine (0.13 mL, 0.9 mmol) was added and the reaction was stirred at room temperature until disappearance of the starting material was noted. The reaction was concentrated to dryness and purified by chromatography (SiO$_2$, 5% EtOAc in hexanes) to afford 43C (72 mg, 95%).

43D. Preparation of 2-(3-chloro-4-methoxybenzamido)-5-phenoxybenzoic acid

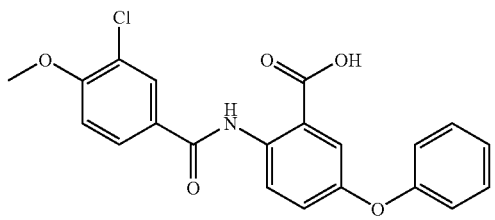

A solution of 43C (60 mg, 0.14 mmol) in THF (2 mL): water (1 mL) at 0° C. was treated with a 1 M solution of LiOH (0.17 mmol). The reaction was warmed to room temperature and stirred for 30 minutes. The solution was neutralized with 1 N HCl and extracted with EtOAc. The combined organic layers were dried (Na$_2$SO$_4$), filtered and concentrated to afford 43D (42 mg, 76%).

43E. Preparation of 2-[(3-chloro-4-methoxybenzoyl)amino]-5-phenoxy-N-(2-phenylethyl)benzamide

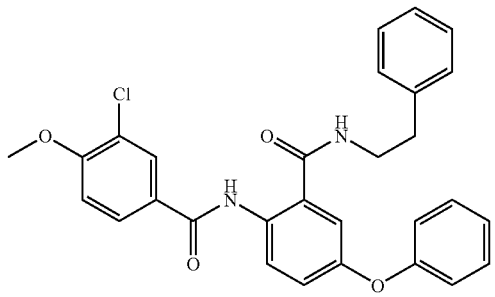

43E

A solution of 43D (17 mg, 0.043 mmol) in DMF (1 mL) was treated with diisopropylcarbodiimide (6 mg, 0.047 mmol) and HOBt (12 mg, 0.086 mmol). The reaction was stirred for 1 hour at room temperature and then phenethylamine (104 mg, 0.86 mmol) was added. The resulting solution was stirred for 3 hours at room temperature, and then concentrated. The crude material was purified by chromatography (SiO$_2$, 5% to 20% EtOAc in Hexanes) to afford 43E (16 mg, 75%). HPLC retention time=4.50 min (YMC S5 ODS 4.6×50 mm, 10-90% aqueous methanol containing 0.2% H$_3$PO$_4$, 4 min gradient, monitored at 220 nm)

Example 44

2-[(3-chloro-4-hydroxybenzoyl)(methyl)amino]-N-isopropyl-5-phenoxybenzamide

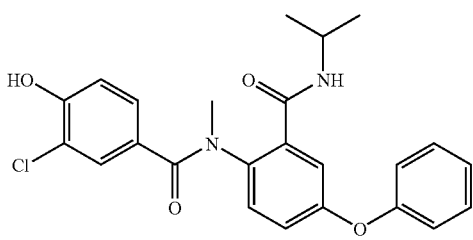

44A. Preparation of 2-formamido-N-isopropyl-5-phenoxybenzamide

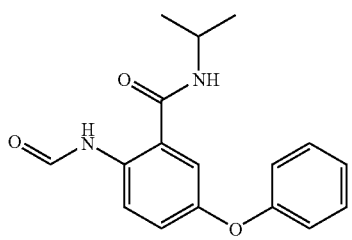

A solution of formic acid (0.02 mL, 0.56 mmol) and acetic anhydride (0.05 mL, 0.56 mmol) was heated to 50° C. for 2 hours under an argon atmosphere. The resulting mixture was diluted with THF (0.2 mL) and added dropwise to a solution of 34B (50 mg, 0.19 mmol) at 0° C. The reaction mixture was slowly warmed to room temperature and stirred for 16 hours. The resulting solution was concentrated to dryness and purified by chromatography (SiO$_2$, 40% EtOAc in hexane) to afford 44A (58 mg, 100%).

44B. Preparation of N-isopropyl-2-(methylamino)-5-phenoxybenzamide

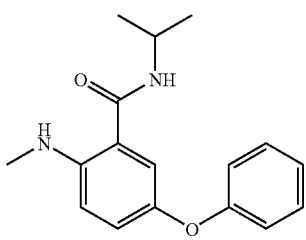

A solution of 44A (55 mg, 0.19 mmol) in THF (1 mL) at 0° C. was treated with BH$_3$.SMe$_2$ (0.09 mL, 0.93 mmol). The resulting yellow solution was warmed to 50° C. for 1 hour, and then cooled to 0° C. and quenched with MeOH (0.25 mL). The resulting solution was treated with acetic acid (0.1 mL) and warmed to 50° C. for 6 hours. The solution was concentrated to dryness and purified by chromatography (SiO$_2$, 10% MeOH in CHCl$_3$) to afford 44B (16 mg).

44C. Preparation of 3-chloro-4-[(3,4-dimethoxyphenyl)methoxy]-N-methyl-N-[2-[[(1-methylethyl)amino]carbonyl]-4-phenoxyphenyl]-benzamide

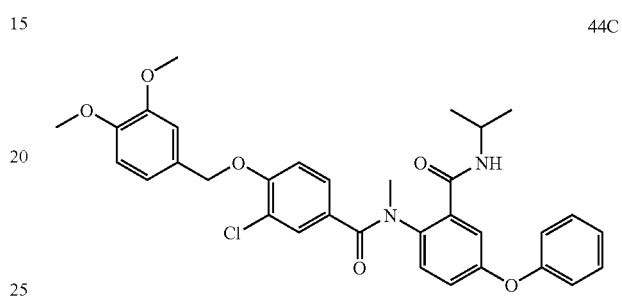

A slurry of 1B (28 mg, 0.09 mmol) and trichloroacetonitrile (0.009 mL, 0.09 mmol) in CH$_2$Cl$_2$ (1 mL) at room temperature was treated with a solution of triphenylphosphine (22 mg, 0.09 mmol) in THF (0.25 mL). The reaction mixture was stirred for 30 minutes and additional trichloroacetonitrile (0.009 mL, 0.09 mmol) and triphenylphosphine (22 mg, 0.09 mmol) were added. The resulting solution was treated with 44B (16 mg, 0.06 mmol) in CH$_2$Cl$_2$ (0.5 mL). The stirring was continued for 2 hours, and then the reaction concentrated to dryness. The residue was purified by chromatography (SiO$_2$, 50% to 75% EtOAc in hexanes) to afford 44C (31 mg).

44D. Preparation of 2-[(3-chloro-4-hydroxybenzoyl)(methyl)amino]-N-isopropyl-5-phenoxybenzamide

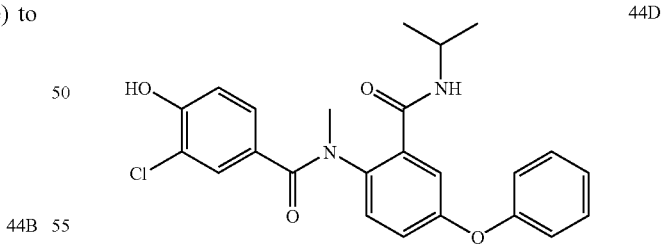

A solution of 44C (30 mg, 0.05 mmol) in CH$_2$Cl$_2$ (1 mL) at 0° C. was treated with TFA (0.05 mL). The solution was warmed to room temperature and stirred for 16 hours. The crude mixture was purified by chromatography (SiO$_2$, 50% EtOAc in hexane) to afford 44D (15 mg, 68%). HPLC Retention Time=3.09 min (YMC ODSA 5 u C18 4.6×50 mm, 10-90% aqueous methanol containing 0.1% TFA, 4 min gradient, monitored at 220 nm) [M+H+]=439.

Example 45

2-[(3-chloro-4-hydroxybenzoyl)amino]-N-[2-(2-methoxyphenyl)ethyl]-5-methylbenzamide

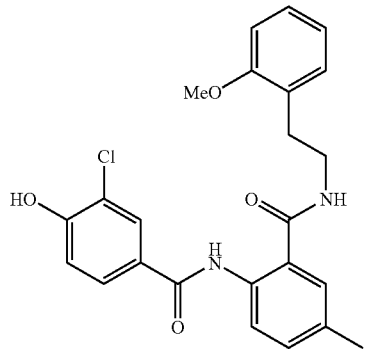

Example 45 was prepared in accordance with the procedure set forth in Example 9, wherein anthranilic ester=methyl 2-amino-5-methylbenzoate and Procedure B described in 9D was utilized. HPLC retention time=1.75 min (Column A). m/z=437.2 (M–H).

What is claimed is:

1. A compound of Formula I:

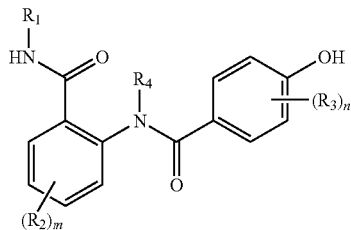

or a pharmaceutically acceptable salt thereof, wherein:
  $R_1$ is —$CH_2CH_2$-(phenyl) or —$CH_2CH_2$-(pyridyl), wherein said phenyl or said pyridyl is optionally substituted with one or two substituents selected from halogen, Me, Et, OMe, and OEt;
  Each $R_2$ is independently selected from alkyl, substituted alkyl, and $OR_{11}$; or one $R_2$ together with another $R_2$ attached to an adjacent carbon may form a fused phenyl ring;
  Each $R_3$ is independently selected from H, halogen, OH, OMe, OEt, SH, Me, Et, $CO_2H$, $NHSO_2Me$, and $NHSO_2Et$; or one $R_3$ together with another $R_3$ attached to an adjacent carbon may form a fused heterocycle;
  $R_4$ is H, Me, Et, or iso-propyl;
  $R_{11}$ is H, alkyl, substituted alkyl, cycloalkyl, substituted cycloalkyl, aryl, or substituted aryl;
  m is 1 or 2; and
  n is 1 or 2.

2. The compound of claim 1 or pharmaceutically acceptable salt thereof, wherein $R_1$ is —$CH_2CH_2$-(phenyl), wherein said phenyl is optionally substituted with one or two substituents selected from halogen, Me, Et, OMe, and OEt.

3. The compound of claim 2 or pharmaceutically acceptable salt thereof, wherein each $R_2$ is independently selected from Me, Et, and $OR_{11}$, wherein $R_{11}$ is H, Me, Et, phenyl, or substituted phenyl; and $R_4$ is H.

4. The compound of claim 2 or pharmaceutically acceptable salt thereof, wherein each $R_3$ is independently selected from halogen, Me, OH, and SH; and n is 1.

5. The compound of claim 3 or pharmaceutically acceptable salt thereof, wherein each $R_3$ is independently selected from halogen, Me, OH, and SH; and n is 1.

6. The compound of claim 1 or pharmaceutically acceptable salt thereof, wherein each $R_3$ is independently selected from halogen, Me, OH, and SH; and n is 1.

7. A pharmaceutical composition comprising at least one compound according to claim 1 or pharmaceutically acceptable salt thereof; and a pharmaceutically-acceptable carrier or diluent.

8. A compound selected from:
  2-[(3-chloro-4-hydroxybenzoyl)amino]-N-[2-(2-methoxyphenyl)ethyl]-5-phenoxybenzamide;
  2-[(3-chloro-4-hydroxybenzoyl)amino]-N-[2-(2-chlorophenyl)ethyl]-5-phenoxybenzamide;
  2-[(3-chloro-4-hydroxybenzoyl)amino]-N-[2-(3-methoxyphenyl)ethyl]-5-phenoxybenzamide;
  2-[(3-chloro-4-hydroxybenzoyl)amino]-5-phenoxy-N-(2-pyridin-2-ylethyl)benzamide;
  2-[(3-chloro-4-hydroxybenzoyl)amino]-N-[2-(4-chlorophenyl)ethyl]-5-phenoxybenzamide;
  2-[(3-chloro-4-hydroxybenzoyl)amino]-5-methoxy-N-[2-(2-methoxyphenyl)ethyl]benzamide;
  2-[(3-chloro-4-hydroxybenzoyl)amino]-N-[2-(3-chlorophenyl)ethyl]-5-phenoxybenzamide;
  N-[2-(2-chlorophenyl)ethyl]-2-[(4-hydroxybenzoyl)amino]-5-phenoxybenzamide;
  2-[(3-chloro-4-hydroxybenzoyl)amino]-N-[2-(2-methoxyphenyl)ethyl]-4-methylbenzamide; and
  2-[(3-chloro-4-hydroxybenzoyl)amino]-N-[2-(2-methoxyphenyl)ethyl]-5-methylbenzamide.

9. The compound of claim 1 or pharmaceutically acceptable salt thereof, wherein $R_1$ is —$CH_2CH_2$-(pyridyl), wherein said pyridyl is substituted with one or two groups selected from H, halogen, Me, Et, OMe, and OEt.

* * * * *

UNITED STATES PATENT AND TRADEMARK OFFICE
CERTIFICATE OF CORRECTION

PATENT NO. : 7,569,725 B2  Page 1 of 1
APPLICATION NO. : 11/255484
DATED : August 4, 2009
INVENTOR(S) : Ellen K. Kick et al.

It is certified that error appears in the above-identified patent and that said Letters Patent is hereby corrected as shown below:

On the Title Page:

Item (73) Assignee: Bristol-Myers Squibb Company, should read

Princeton, NJ (US)

Claim 8, column 46, at line 32 insert
-- 2-[(3-chloro-4-hydroxybenzoyl)amino]-5-phenoxy-$N$-(2-phenylethyl)benzamide;
2-[(3-chloro-4-hydroxybenzoyl)amino]-$N$-[2-(4-methoxyphenyl)ethyl]-5-phenoxybenzamide; --.

Signed and Sealed this

Fourth Day of May, 2010

David J. Kappos
*Director of the United States Patent and Trademark Office*